Figure 1:
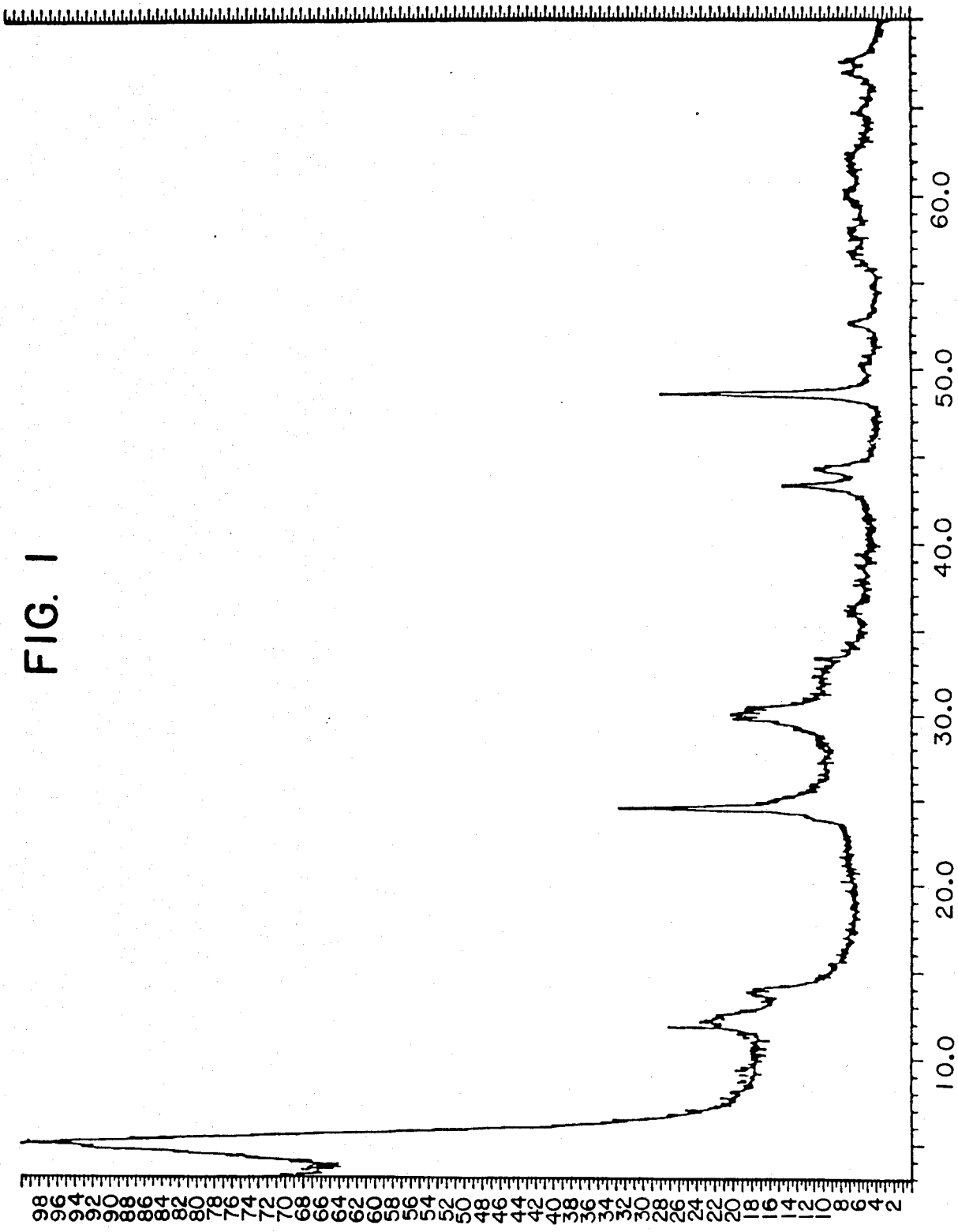

United States Patent [19]

Landis et al.

[11] Patent Number: 4,859,648

[45] Date of Patent: Aug. 22, 1989

[54] LAYERED METAL CHALCOGENIDES CONTAINING INTERSPATHIC POLYMERIC CHALCOGENIDES

[75] Inventors: Michael E. Landis, Woodbury; Pochen Chu, West Deptford; Ivy D. Johnson, Mt. Laurel; Garry W. Kirker, Washington Twp., Warren County, all of N.J.; Mae K. Rubin, Bala Cynwyd, both of Pa.

[73] Assignee: Mobil Oil Corporation, New York, N.Y.

[21] Appl. No.: 879,787

[22] Filed: Jun. 27, 1986

Related U.S. Application Data

[63] Continuation-in-part of Ser. No. 687,414, Dec. 28, 1984, abandoned.

[51] Int. Cl.$^4$ .................... B01J 21/06; B01J 21/02; B01J 21/16
[52] U.S. Cl. ................................ 502/242; 502/84; 502/202; 502/350
[58] Field of Search ............ 502/242, 350, 77, 63, 502/84; 423/70, 71

[56] References Cited

U.S. PATENT DOCUMENTS

| | | | |
|---|---|---|---|
| 3,063,807 | 11/1962 | Kenworthy | 423/70 |
| 3,244,643 | 4/1966 | Schwartz | 502/64 |
| 4,248,739 | 2/1981 | Vaughan et al. | 252/455 R |
| 4,367,163 | 1/1983 | Pinnavaia et al. | 252/455 R |
| 4,410,637 | 10/1983 | Kortbeek et al. | 518/714 |
| 4,510,257 | 4/1985 | Lewis et al. | 502/63 |
| 4,579,832 | 4/1986 | Shabtai et al. | 502/84 |
| 4,593,013 | 6/1986 | Jacobson et al. | 502/167 |
| 4,600,503 | 7/1986 | Angevine et al. | 208/251 H |
| 4,629,713 | 12/1986 | Suzuki et al. | 502/84 |
| 4,637,991 | 1/1987 | Battiste et al. | 502/84 |
| 4,637,992 | 1/1987 | Lewis et al. | 502/84 |
| 4,650,779 | 3/1987 | Goldstein | 502/38 |

FOREIGN PATENT DOCUMENTS

| | | |
|---|---|---|
| 0110628 | 11/1983 | European Pat. Off. |
| 0159756 | 4/1985 | European Pat. Off. |
| 2071071 | 9/1981 | United Kingdom ............ 423/71 |
| 8503015 | 7/1985 | United Kingdom . |
| 8503016 | 7/1985 | United Kingdom . |

OTHER PUBLICATIONS

Weiss et al., Angew. Chem./72 Jahrg' 1960/Nr/2, pp. 413–415.

*Primary Examiner*—Carl F. Dees
*Attorney, Agent, or Firm*—Alexander J. McKillop; Charles J. Speciale; Laurence P. Hobbes

[57] ABSTRACT

Layered chalcogenide materials of high thermal stability and surface area which contain interspathic polymeric chalcogenides such as polymeric silica are prepared by ion exchanging a layered metal oxide, such as layered titanium oxide, with organic cation, to spread the layers apart. A compound such as tetraethylorthosilicate, capable of forming a polymeric oxide, is thereafter introduced between the layers. The resulting product is treated to form polymeric oxide, e.g. by hydrolysis, to produce the layered oxide material. The resulting product may be employed as catalyst material in the conversion of organic compounds.

103 Claims, 3 Drawing Sheets

LAYERED METAL CHALCOGENIDES CONTAINING INTERSPATHIC POLYMERIC CHALCOGENIDES

This application is a continuation-in-part of U.S. application Ser. No. 687,414, filed Dec. 28, 1984 (and now abandoned), the entire contents of which are incorporated herein by reference.

The present invention relates to layered metal chalcogenides containing interspathic polymeric chalcogenides as well as a method for preparing the same. The invention also is concerned with a catalytic composition comprising the layered metal chalcogenide material as well as catalytic conversion of an organic feedstock in the presence thereof. More particularly, the invention relates to layered metal oxides which contain interspathic metal oxides, e.g., layered titanium oxides which contain interspathic silica. For the purposes of the invention, the term "metal" can be considered to include the elements boron, silicon, phosphorus and arsenic.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

Various approaches have been taken to provide layered materials of enhanced interlayer distance having thermal stability. Most techniques rely upon the introduction of an inorganic "pillaring" agent between the layers of a layered material. For example, U.S. Pat. No. 4,216,188 incorporated herein by reference discloses a clay which is cross-linked with metal hydroxide prepared from a highly dilute colloidal solution containing fully separated unit layers and a cross-linking agent comprising a colloidal metal hydroxide solution. However, this method requires a highly dilute forming solution of the clay (less than 1 g/l) in order to effect full layer separation prior to incorporation of the pillaring species, as well as positively charged species of cross linking agents. U.S. Pat. No. 4,248,739, incorporated herein by reference, elates to stable pillared interlayered clay prepared from smectite clays reacted with cationic metal complexes of metals such as aluminum and zirconium. The resulting products exhibit high interlayer separation and thermal stability.

U.S. Pat. No. 4,176,090, incorporated herein by reference, discloses a clay composition interlayered with polymeric cationic hydroxy metal complexes of metals such as aluminum zirconium and titanium. Interlayer distances of up to 16 A are claimed although only distances restricted to about 9 A are exemplified for calcined samples. These distances are essentially unvariable and related to the specific size of the hydroxy metal complex.

Silicon-containing materials are believed to be a highly desirable species of intercalating agents owing to their high thermal stability characteristics. U.S. Pat. No. 4,367,163, incorporated herein by reference, describes a clay intercalated with silica prepared by impregnating a clay substrate with a silicon-containing reactant such as an ionic silicon complex, e.g., silicon acetylacetonate, or a neutral species such as $SiCl_4$. The clay may be swelled prior to or during silicon impregnation with a suitable polar solvent such as methylene chloride, acetone, benzaldehyde, tri- or tetraalkylammonium ions, or dimethylsulfoxide. This method, however, appears to provide only a monolayer of intercalated silica resulting in a product of small spacing between layers, about 2–3 A as determined by X-ray diffraction.

In one aspect, the present invention resides in a layered product comprising a layered chalcogenide of at least one element having an atomic number of 4, 5, 12 to 15, 20 to 33, 38 to 51, 56 to 83 and greater than 90, inclusive, and an interspathic polymeric chalcogenide of at least one element selected from Group IVB of the Periodic Table of the Elements (Fisher Scientific Co. Cat. No. 5-702-10, 1978), separating the chalcogenide layers, said product having a d-spacing of at least 20A. Preferably, such materials can be thermally stable, i.e., capable of withstanding calcining at a temperature of about 450° C. for at least 2 hours without significant reduction (e.g., not greater than 10 or 20%) in the spacing between the chalcogenide layers.

In another aspect, the invention resides in a layered product comprising a non-swellable (as defined herein) layered chalcogenide of an element ranging in atomic number from 13 to 15, 21 to 33, 39 to 51, 57 to 83 and greater than 90, inclusive, and an interspathic polymeric oxide separating the chalcogenide layers.

For purposes of the present invention the term "chalcogenide" includes members of the group consisting of oxides, sulfides, selenides, tellurides, and polonides of elements other than those of Group VIB. Oxides are particularly preferred chalcogenides of the present invention, both as the interspathic polymeric chalcogenide and the layered chalcogenides. For present purposes, polymeric chalcogenides are considered to include chalcogenides of two or more repeating units preferably three or more repeating units, say four or more or even five or more repeating units. The extent of polymerization of the interspathic polymeric chalcogenide is believed to affect the ultimate interlayer separation of the layered product.

The method of the present invention is particularly useful in preparing a layered material of a desired interlayer spacing. The interlayer spacing of the layered material can be tailored by careful selection of the "propping" agent used to separate the layers during treatment with the interspathic polymeric chalcogenide precursors which are eventually converted to the thermally stable polymeric chalcogenide "pillars." Indeed, a wide range of interlayer spacings can be achieved in preparing layered materials of the present invention. Interlayer distances can range anywhere from 2 to 30 angstroms or more, say, e.g., greater than 5, 10, 15 or 20 angstroms, depending largely on the type of "propping" agent used as well as the layered chalcogenide being treated.

In another aspect, the invention resides in a layered titanate composition having interspathic polymeric silica between the titanate layers and having the characteristic X-ray diffraction pattern of Table 1 below.

TABLE 1

COMPOSITE LIST OF PRINCIPAL X-RAY POWDER DIFFRACTION PEAKS FOR SILICOTITANATES

| Line Number | 2 Theta min–2 Theta max* | $I/I_{Relative}$ Intensity) Range** |
|---|---|---|
| 1 | less than or equal to 8.7 | VS to W |
| 2 | 11.1–14.3 | S to W |
| 3 | 11.8–15.2 | M to W |
| 4 | 24.5–25.0 | VS to W |
| 5 | 25.0–25.4 | M to W |
| 6 | 28.5–30.2 | VS to W |
| 7 | 29.8–30.6 | S to W |
| 8 | 33.0–33.5 | S to W |
| 9 | 43.2–43.5 | M to W |
| 10 | 44.2–44.7 | M to W |
| 11 | 48.5–48.9 | VS to M |
| 12 | 52.7–52.9 | W |

*2 Theta min–2 Theta max = Range of 2 Theta values observed for eight specific pillared silicotitanates.
**These values were determined by standard techniques.

The radiation was the K-alpha doublet of copper, and a scintillation counter spectrometer was used. The peak heights, I, and the positions as a function of 2 times theta (2 theta), where theta is the Bragg angle, were determined. From these, the relative intensities, $I/I_o$ where $I_o$ is one hundredth of the intensity of the strongest line or peak, and d is the interplanar spacing in angstroms (A), corresponding to the recorded lines, were calculated. The relative intensity in the table above is expressed as follows:

| Relative Intensity | $I/I_o$ |
|---|---|
| VS (Very Strong) | 60–100 |
| S (Strong) | 40–60 |
| M (Medium) | 20–40 |
| W (Weak) | 0–20 |

Minor variations in the interplanar spacing and relative intensity may occur as a result of ion exchange, changes in the composition of the silicotitanate, or exposure to calcination conditions.

In one aspect, the present invention relates to a method for preparing a layered material containing an interspathic polymeric chalcogenide of at least one element selected from Groups IB, IIB, IIIA, IIIB, IVA, IVB, VA, VB, VIA, VIIA, and VIIIA of the Periodic Table. The method comprises: treating a layered chalcogenide of at least one element having an atomic number of 4, 5, 12 to 15, 20 to 33, 38 to 51, 56 to 83 and greater than 90, inclusive, which contains ion exchange sites having interspathic cations associated therewith, with an organic compound which is a cationic species or capable of forming a cationic species to effect exchange with said interspathic cations. An electrically neutral compound capable of conversion to the interspathic polymeric chalcogenide is provided between the layers of the treated layered chalcogenide. The compound is then converted to the interspathic polymeric chalcogenide to form the layered material.

In another aspect, the invention resides in a method for preparing a layered product having adjacent layers separated by an interspathic polymeric chalcogenide of at least one element selected from Groups IB, IIB, IIIA, IIIB, IVA, IVB, VA, VB, VIA, VIIA, and VIIIA of the Periodic Table, which method comprises starting with a layered chalcogenide material of at least one element having an atomic number of 4, 5, 12 to 15, 20 to 33, 38 to 51, 56 to 83 and greater than 90, said layered chalcogenide material having anionic sites associated therewith; physically separating the layers of the chalcogenide material by introducing an organic cationic species between the layers at said anionic sites; providing between the separated layers of said layered chalcogenide at least one neutral compound capable of conversion to polymeric chalcogenide; and converting said compound to the polymeric chalcogenide to produce a layered product having adjacent layers separated by an interspathic polymeric chalcogenide. For present purposes, the compound capable of conversion to polymeric chalcogenide can be a mixture of materials, e.g., a zeolite reaction mixture.

In yet another aspect, the invention resides in treating a layered silicic acid, e.g., a high silica alkali silicate such as synthetic magadiite, or synthetic kenyaite. These materials which are composed of only tetrahedral sheets condensed on each other and which lack an octahedral sheet can be prepared by co-crystallizing in the presence of one or more elements selected from Groups IB, IIA, IIB, IIIB, IVA, IVB, VA, VB, VIA, VIIA and VIII of the Periodic Chart, most preferably from the group consisting of Al, Zr, B, Cr, Fe, Ga, In and Ni, which contains the above-discussed interspathic polymeric chalcogenide. Preferably said polymeric chalcogenide is polymeric silica or a mixture of polymeric silica and polymeric alumina. The invention further comprises a method of preparing these materials.

In another aspect, the invention resides in a process for ion-exchanging residual cations, present in the layered product having adjacent layers separated by interspathic polymeric chalcogenide. Such ion-exchange includes exchange of sodium or other alkali metal ions with other cations, e.g., monovalent, divalent, trivalent or even tetravalent cations.

The present invention can also be described as relating to a method for preparing layered materials which comprise a layered chalcogenide of at least one element having atomic numbers of 4, 5, 12 to 15, 20 to 33, 38 to 51, 56 to 83 and greater than 90, inclusive. The layered chalcogenide comprises between its layers an interspathic polymeric chalcogenide of at least two atoms of at least one element selected from Groups IB, IIB, IIIA, IIIB, IVA, IVB, VA, VB, VIA, VIIA and VIIIA of the Periodic Table. This polymeric chalcogenide may be in amorphous or crystalline, e.g. zeolite, form. The present invention is particularly useful in that it permits the preparation of layered chalcogenide materials of relatively high interplanar distance (d-spacing), e.g., greater than about 10, 15, 18, 20, 25, or even 30 or more angstroms. These materials are capable of being exposed to severe conditions such as those encountered in calcining, e.g., at temperatures of about 450° C. for about two or more hours, e.g., four hours, in nitrogen or air, without significant decrease, say, e.g., less than about 10%, in interlayer distance. Furthermore, such layered chalcogenides can be prepared without the severe dilution often necessary to introduce the interspathic material in prior art techniques of interlayering. Finally, the size of interspathic polymeric chalcogenide contained within the final product can be greatly varied because the polymeric chalcogenide precursor species are introduced in an electrically neutral form such that the amount of interspathic material incorporated within the layered chalcogenide is not dependent upon the charge density of the original layered chalcogenide. Charge density should be taken into consideration in determining the suitability of the cationic species introduced between the layers in the procedure used to prop open the layers prior to pillaring. The use of an electrically neutral polymeric chalcogenide precursor allows the formation of materials with widely varying interlayer spacing, further distinguishing the present invention over the prior art. Preferably, said layered chalcogenide is a layered oxide and said interspathic polymeric chalcogenide is an interspathic polymeric oxide.

The method of the present invention utilizes a layered chalcogenide starting material which contains ion exchange sites having interspathic cations associated therewith. Such interspathic cations may include hydrogen ion, hydronium ion and alkali metal cation. The starting material is treated with a "propping" agent comprising a source of organic cation such as organoammonium, which source may include the cation itself, in order to effect an exchange of the interspathic cations resulting in the layers of the starting material being propped apart. Often, alkylammonium cations include n-dodecylammonium, n-heptylammonium, n-hexylammonium and n-propylammonium. The source of organic cation in those instances where the interspathic cations include hydrogen or hydronium ions may include a neutral compound such as organic amine which is converted to a cationic analogue during the "propping" treatment. The organic cation should be capable of displacing or supplanting the original interspathic cations. In some instances, it may be desirable to remove excess propping agent which is not electrostatically bound within the layered starting material in order to permit the addition of greater amounts of polymeric chalcogenide precursor. Such removal may be effected by washing out the propping agent with a material which is soluble with said propping agent. The foregoing treatment can result in the formation of a layered metal chalcogenide of enhanced interlayer separation depending upon the size of the organic cation introduced. In one embodiment, a series of organic cation exchanges can be carried out. For example, an organic cation may be exchanged with an organic cation of greater size, thus increasing the interlayer separation in a step-wise fashion. In other words, an interspathic source of organic cation is exchanged with a source of a larger organic cation. Contact of the layered oxide with the propping agent may be conducted in aqueous medium so that water is trapped between the layers of the "propped" chalcogenide.

After the ion exchange, the organic-"propped" species is treated with a compound capable of forming the above-described polymeric chalcogenide. Preferably, such compounds are capable of forming the polymeric chalcogenide upon hydrolysis or other polymerizing reactions. Hydrolyzable compounds are well-suited as such compounds. It is preferred that the organic cation deposited between the layers be capable of being removed from the layered chalcogenide material; without substantial disturbance or removal of the interspathic polymeric chalcogenide. For example, organic cations such as n-octylammonium may be removed by exposure to elevated temperatures, e.g., calcination, in nitrogen or air or chemical oxidation conditions, preferably after the interspathic polymeric chalcogenide precursor has been converted to the polymeric chalcogenide in order to form the layered material of the present invention.

The polymeric chalcogenide precursor-containing product can be exposed to suitable conversion conditions, such as hydrolysis and/or calcination to form the layered material of the present invention. The hydrolysis step may be carried out by any method, for example, by interspathic water already present in organic-"propped" layered chalcogenide material. Because of the effect of interspathic water on hydrolysis, the extent of hydrolysis may be modified by varying the extent to which the organic-"propped" species is dried prior to addition of the polymeric chalcogenide precursor. As noted earlier, the product]after conversion to the polymeric chalcogenide form may be exposed to conditions which remove organic compounds such as the organic cation propping agents, e.g., exposure to elevated temperatures such as those encountered by calcining in air or nitrogen.

The products of the present invention, especially when calcined, exhibit high surface area, e.g., greater than 200, 300, 400 or even 600 $m^2/g$, and thermal and hydrothermal stability making them highly useful for hydrocarbon conversion processes as catalysts or catalytic supports, for example, cracking and hydrocracking.

As noted above, layered chalcogenides of elements ranging in atomic number of 4, 5, 12 to 15, 20 to 33, 38 to 51, 56 to 83 and greater than 90, inclusive, may be employed as starting materials of the present invention. Included are oxides of aluminum and silicon such as clays. Layered clays such as bentonite may be treated in accordance with the present invention. Preferably, however, the layered chalcogenide is "non-swellable" which is intended to distinguish from conventional clays which contain octahedrally coordinated metal oxide sheets bonded to tetrahedrally coordinated silica sheets and which undergo substantial swelling, sometimes by an essentially unbounded amount, when contacted with water. As used herein in relation to a layered chalcogenide material, the term "non-swellable" is defined as meaning a layered chalcogenide material, which, when contacted with at least 10 grams of water per gram of the layered chalcogenide at 23° C. for 24 hours, exhibits an increase in d-spacing no greater than 5 Å as compared with the material before treatment. Included among these materials are $H_2Ti_3O_7$, $Na_2Ti_3O_7$ and $KTiNbO_5$ as well as certain layered silicates, for example, the metasilicates. Layered silicates, e.g., high silica alkali silicates such as magadiite, natrosilite, kenyaite, makatite, nekoite, kanemite, okenite, dehayelite, macdonaldite and rhodesite, unlike swellable clays, lack octahedral sheets, i.e., sheets composed of atoms which are octahedrally coordinated with oxygen atoms. Such high silica alkali silicates may be utilized as starting materials in the present invention as well as synthetic analogues thereof. Without stable intercalated pillars, these materials tend to have collapsed layers at elevated temperatures, low porosity and low surface area. In some cases it has been found preferable that these layered clays or silicates be treated by contacting with one or more polar organic solvents or water prior to or during exchange with the source of organic cation. The polar organic solvent used should exhibit electric dipole moments in the gas phase of at least 3.0 Debyes (D), preferably at least 3.5 Debyes, say at least about 3.8D. Examples of suitable organic solvents are dimethylsulfoxide (DMSO) and dimethylformamide (DMF). A table of selected organic compounds and their electric dipole moments can be found in CRC Handbook of Chemistry and Physics, 61st Edition, 1980-1981 at pages E-64 to E-66, incorporated herein by reference. The intercalation of synthetic magadiite with organic liquids such as DMSO, followed by treatment with alkylamines is discussed in *American Mineralogist*, Volume 60, pages 650-658, 1975, incorporated herein by reference. It is believed that the treatment of any starting material with one or more highly polar solvents can be efficacious in facilitating the introduction of the source of organic cation between the layers of starting material. d-Spacings greater than 10, 15, 20, 25 or even 30 may be obtained by this method.

In one preferred embodiment, the starting material is a layered chalcogenide, preferably oxide, of Group IV A metal such as titanium, zirconium and hafnium, with a layered titanate, e.g., a trititanate such as $Na_2Ti_3O_7$, being particularly preferred. Trititanates are commercially available materials whose structure consists of anionic sheets of titanium octahedra with interlayer alkali metal cations which can be exchanged for interspathic $H^+$ and $H_3O^+$ ions. A method for making such material may be found in U.S. Pat. No. 2,496,993, incorporated herein by reference. It is known that the interlayer distance of $Na_2Ti_3O_7$ may be increased by replacing interlayer sodium ions with larger octylammonium ions. See, Weiss et al., Angew. Chem/72 Jahrg. 1960/Nr/2, pp 413-415. However, the organic-containing trititanate is highly susceptible to heat which can remove the organic material and cause collapse of the layered structure. The present invention serves to introduce a stable polymeric chalcogenide, preferably a polymeric oxide comprising an element selected from the group consisting of silicon, germanium, tin and lead, e.g., polymeric silica, between adjoining layers resulting in a heat-stable material which substantially retains its interlayer distance upon calcination.

Such layered silicotitanate compositions having interspathic polymeric silica between the titanate layers have been found useful in the oligomerization of low molecular weight olefins ($C_3$ to $C_5$), e.g. propylene, to form hydrocarbons boiling in the gasoline or light distillate range (about 66° to 260° C. (150° to 500° F.), preferably about 93° to 232° C. (200° to 450° F.), at atmospheric pressure). Layered titanate materials containing an exchangeable cation between the layers such as an alkali metal ion, e.g. sodium ion, may be treated by exchange with (1) ammonium ion or (2) hydrogen ion and/or (3) calcination to form a proton-exchanged material which may be at least partially exchanged with replacement cations such as cesium, cerium, cobalt, nickel, copper, zinc, manganese, platinum, lanthanum, aluminum, ammonium, hydronium and mixtures thereof. Ni(II) and Al(III) cations are of particularly significant interest as replacement cations. Layered titanates prepared without appreciable alkali metal content, e.g. by exchanging out the alkali metal with acid treatment, are also particularly well suited to such oligomerizations. Such materials have an alkali metal content below about 1.0 weight percent, preferably below about 0.5 weight percent.

The operating conditions employed for such oligomerization to gasoline and light distillate boiling range components may include carrying out the conversion of the olefins in the vapor-phase by contact in a reaction zone, such as, for example, a fixed bed of catalyst composition, under conversion effective conditions. This process may be conducted in either batch or fluid bed operation with attendant benefits of either operation readily obtainable.

The present improved process may be carried out at a temperature between about 232° to 427° C. (450° and 800° F.), preferably from about 260° to about 399° C. (about 500° to about 750° F.), and at pressures ranging from about atmospheric up to about 1000 psig, preferably from about atmospheric to about 450 psig. The weight hourly space velocity (WHSV) may be maintained at from about 0.2 $hr^{-1}$ to about 20 $hr^{-1}$, preferably from about 0.5 $hr^{-1}$ to about 4 $hr^{-1}$. The amount of co-fed water can range from about 0 to about 5 moles of water/mole of olefin feedstock. Within these limits the conditions of temperature and pressure will vary considerably depending upon equilibrium considerations, exact feed material, and presence or absence of diluents, such as, for example, $C_1$-$C_4$ paraffins, such as methane, ethane, propane, isobutane and n-butane; and hydrogen sulfide. Optimum conditions are those in which maximum yields of gasoline or light distillate component products are obtained and hence considerations of temperature and pressure will vary within a range of conversion levels designed to provide the highest selectivity and maximum yield.

The preferred starting feed materials for the process are olefins of from 3 to 5 carbon atoms, such as, for example, propylene. The feedstock may be comprised of a single olefin or a mixture of different olefins.

The amount of diluent which may be present in the improved process of this invention is not narrowly critical and may vary within the range of 0 to about 90 weight percent based on the weight of olefin feedstock. Preferably, the amount of diluent is within the range of from about 20 to about 60 weight percent.

Additional information on suitable process conditions may be found in U.S. Pat. No. 4,150,062 incorporated herein by reference.

The above silica-intercalated layered titanate compositions may also be used to oligomerize intermediate molecular weight olefins, $C_6$ to $C_{20}$, preferably $C_{10}$ to $C_{16}$, in order to form hydrocarbons boiling in the heavy distillate to lube range (about 260° to 566° C. (500° to 1050° F.), preferably about 316° to 454° C. (600° to 850°

F.), i.e., $C_{20}+$ hydrocarbons. Process conditions in a sealed reactor can be adjusted to favor the formation of $C_{20}+$ materials by using moderate reaction temperatures of about 140° to 285° C. depending on the olefin feed used, at about autogenous pressures during contact with the layered titanate composition. When feeds of 1-decene are employed said temperatures range from about 140° to 160° C. When feeds of 1-hexadecene are used, reaction temperatures of about 265° to 285° C. are preferred. Oligomerization conditions which may be applied to the oligomerization of intermediate molecular weight olefins to many distillates and lubes may be found in U.S. Pat. No. 4,542,247, incorporated herein by reference.

In another preferred embodiment, the chalcogenide starting material is a layered silicate lacking octahedral sheets, either in natural or synthetic form, such as magadiite, kenyaite or makatite, which may contain elements capable of tetrahedral coordination other than silicon in its framework, e.g., Al, B, Cr, Fe, Ga, In, Ni, Zr or other catalytically useful metals.

As previously stated, the starting layered chalcogenide material is treated with an organic compound capable of forming cationic species such as organophosphonium or organoammonium ion, before adding the polymeric chalcogenide source. Insertion of the organic cation between the adjoining layers serves to physically separate the layers in such a way as to make the layered chalcogenide receptive to the interlayer addition of an electrically neutral, hydrolyzable, polymeric chalcogenide precursor In particular, alkylammonium cations have been found useful in the present invention. Thus $C_3$ and larger alkylammonium, e.g., n-octylammonium, cations are readily incorporated within the interlayer species of the layered chalcogenides, serving to prop open the layers in such a way as to allow incorporation of the polymeric chalcogenide precursor. The extent of the interlayer spacing can be controlled by the size of the organoammonium ion employed so that use of the n-propylammonium cation can achieve a d-spacing of about 2 to 5 A or an opening of about 2-3 A, whereas to achieve an interlayer opening of 10 to 20 A an n-octylammonium cation or a cation of equivalent length is required. The interlayer spacing obtained by each cation can also vary depending on the layered metal chalcogenide being treated. Indeed, the size and shape of the organic cation can affect whether or not it can be incorporated within the layered chalcogenide structure at all. For example, bulky cations such as tetrapropylammonium are generally undesirable for use in the present method while ammonium cations derived from n-alkyl primary amines, such as primary monoamines, are preferred. The organic ammonium cations separating the chalcogenide layers may also be formed in situ by reaction of the neutral amine species with interlayer hydrogen or hydronium cations of the layered chalcogenide starting material. Alternatively, where the interlayer cations of the layered chalcogenide starting material are alkali metal cations, the organic ammonium cation may be formed by initially combining an amine and an aqueous acid solution, such as hydrochloric acid, and then treating the layered chalcogenide with the resulting aqueous organoammonium ion solution. In either case, the treatment can be conducted in aqueous media so that water is then available to hydrolyze the electrically neutral, hydrolyzable polymeric chalcogenide precursor subsequently introduced into the "propped" product. Upon hydrolysis, the polymeric chalcogenide precursor forms a thermally stable polymeric chalcogenide. A final calcination step may be employed which is severe enough to remove a substantial amount of the organic interspathic species. Any remaining organic can be removed by a separate chemical treatment. Preferably, the layered chalcogenide starting material is a layered oxide whilst the polymeric chalcogenide source is a polymeric oxide source.

The interspathic polymeric chalcogenide pillars formed between the layers of the chalcogenide starting material may include a chalcogenide, preferably oxide, of zirconium or titanium or more preferably of an element selected from Group IVB of the Periodic Table (Fischer Scientific Company Cat. No. 5-702-10, 1978), other than carbon, i.e., silicon, germanium, tin and lead. Other such elements may include those of Group VA, e.g., V, Nb, and Ta, those of Group IIA, e.g., Mg or those of Group IIIB, e.g., B. Most preferably, the pillars include polymeric silica. In addition, the polymeric chalcogenide pillars may include an element which provides catalytically active acid sites in the pillars, preferably aluminum.

The polymeric chalcogenide pillars are formed from a precursor material which is preferably introduced between the layers of the organic "propped" species as a cationic, or more preferably, electrically neutral, hydrolyzable compound of the desired elements, e.g., those of Group IVB. The precursor material is preferably an organometallic compound which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Where the pillars are also required to include polymeric alumina, a hydrolyzable aluminum compound can be contacted with the organic "propped" species before, after or simultaneously with the contacting of the layered chalcogenide with the silicon compound. Preferably, the hydrolyzable aluminum compound employed is an aluminum alkoxide, e.g., aluminum isopropoxide. If the pillars are to include polymeric titania, a hydrolyzable titanium compound such as titanium alkoxide, e.g., titanium isopropoxide, may be used. In addition, the polymeric oxide precursor may contain zeolite precursors such that exposure to conversion conditions results in the formation of interspathic zeolite material as at least some of the polymeric chalcogenide.

After hydrolysis to produce the polymeric chalcogenide pillars and calcination to remove the organic propping agent, the final pillared product may contain residual exchangeable cations. For example, sodium titanate pillared with polymeric silica may contain 2-3% or more of weight of residual sodium. Such residual cations in the layered material can be ion exchanged by known methods with other cationic species to provide or alter the catalytic activity of the pillared product. Suitable replacement cations include cesium, cerium, cobalt, nickel, copper, zinc, manganese, platinum, lanthanum, aluminum, ammonium, hydronium and mixtures thereof.

The layered silicates treated by the present invention known as high silica alkali silicates whose layers lack octahedral sheets can be prepared hydrothermally from an aqueous reaction mixture containing silica and caustic at relatively moderate temperatures and pressures. These layered silicates may contain tetracoordinate framework atoms other than Si. Such layered silicates can be prepared by co-crystallizing in the presence of non-silicon tetravalent elements, e.g. those selected from the group consisting of Al, B, Cr, Fe, Ga, In, Ni, Zr as well as any other such elements which are catalytically useful when incorporated in the silicate structure. Alternatively, non-silicon framework elements already in a layered silicate may be substituted by a tetracoordinate element. For example, kenyaite containing boron in its framework when treated with aluminum nitrate results in a kenyaite which contains aluminum in its framework. Both co-crystallized and substituted layered high silica alkali silicates may be treated by the present invention to provide layered materials containing interspathic polymeric chalcogenides.

Another aspect of the present invention resides in preparing synthetic magadiite-type materials which contain interspathic polymeric oxides. Synthetic magadiite is readily synthesized hydrothermally from a reaction mixture containing inexpensive sources of silica and caustic. Tetracoordinate elements other than silicon, e.g., those selected from the group consisting of Al, B, Cr, Fe, Ga, In, Ni, Zr and other catalytically useful metals, may be added to the reaction mixture to produce synthetic magadiite-type layered silicates. Preferably, such elements are selected from the group consisting of Al and Fe. An organic directing agent may also be added to the reaction mixture. The reaction mixture for synthetic magadiite-type materials can be described in molar ratios as follows:

| | |
|---|---|
| $SiO_2/X_2O_3 =$ | 10 to infinity where X can be Al, B, Cr, Fe, Ga, and/or Ni or other catalytically useful metal |
| $M^+OH^-/SiO_2 =$ | 0 to 0.6, (preferably 0.1–0.6) M = any alkali metal |
| $H_2O/SiO_2 =$ | 8–500 |
| $R/SiO_2 =$ | 0–0.4 | where R can be an organic such as benzyltriethylammonium chloride, benzyltrimethylammonium chloride, dibenzyldimethylammonium chloride, N,N'-dimethylpiperazine, triethylamine, or other quaternary compounds or heterocyclic amines. The reaction mixture can be maintained at a temperature of about 100° to 200° C. for anywhere from about 1 to 150 days in order to form a product having the following composition:

| | |
|---|---|
| % N = | 0–3, e.g., 0 to 0.3 |
| $SiO_2/X_2O_3 =$ | 10 to infinity where X may be in the tetrahedral or octahedral position |
| $M_2O/SiO_2 =$ | 0 to 0.5, e.g., 0.05–0.1 |

The synthetic layered silicate materials thus prepared are of low surface area. Introduction of interspathic polymeric oxides according to the method of the present invention can increase the surface area of these materials. Generally, the synthetic magadiite-type material is acidified by any suitable means, e.g., treatment with aqueous 0.1N HCl, and thereafter treated with a "propping" agent, alone or combined with a suitable polar solvent as discussed above. A suitable compound capable of conversion to a polymeric oxide is combined with the "propped" layered silicate. The resulting material may then be calcined to remove residual organics.

Another aspect of the present invention resides in preparing synthetic kenyaite-type materials which contain interspathic polymeric oxides. Kenyaite, a layered silicic acid which is known to exist in nature as a sodium salt $Na_2Si_{22}O_{45}H_2O$ can be prepared in the potassium form $K_2Si_{22}O_{45}10H_2O$ in the laboratory. Synthetic kenyaite is readily synthesized hydrothermally from a reaction mixture containing inexpensive sources of silica and caustic, preferably KOH. Tetracoordinate elements other than silicon, e.g., those selected from the group consisting of Al, B, Cr, Fe, Ga, In, Ni, Zr and other catalytically useful metals, may be added to the reaction mixture to produce synthetic kenyaite-type layered silicates. $Al(NO_3)_3 \cdot 9H_2O$ and aluminum-tri-sec-butoxide are suitable reagents for the introduction of non-silicon tetracoordinate elements in the kenyaite framework. Co-crystallizing with B, Al, and/or Zr is particularly preferred. The reaction mixture may also be seeded with kenyaite. The resulting layered silicates can then be treated in accordance with the present invention.

The present invention further contemplates an embodiment wherein the source of organic cation exchanged with the interspathic cations comprises a zeolite synthesis directing agent. Preferably, this embodiment places sources of alumina and alkali metal between the layers of the treated layered chalcogenide. These sources can be introduced along with the compound capable of conversion to the interspathic polymeric chalcogenide such as tetraethylorthosilicate. Upon exposure to zeolite crystallization conditions, a layered material comprising interspathic zeolite, e.g. ZSM-5, is formed. Sources of organic cation may include primary monoalkylamines or primary monoalkylammonium ions such as n-octylamine or n-octylammonium ion. Suitable sources of alumina include sodium aluminate aluminum sulfate and alumina while suitable sources of alkali metal include alkali metal hydroxide such as sodium hydroxide. U.S. Pat. No. 4,151,189 incorporated herein by reference, discloses reagents and conditions suitable in forming zeolite component of this embodiment. The patent oxides of aluminum, silicon and alkali metal suitable for synthesis as well as zeolite synthesis directing such as sources of organic nitrogen cation, like $C_4$–$C_{10}$ n-alkylamines. Suitable reaction conditions include heating the layered material containing the zeolite precursors to a temperature of from about 99° C. to about 260° C. for a period from about 6 hours to 60 days, preferably about 149° C. to about 232° C. for a period from about 12 hours to 8 days. The resulting layered material comprising interspathic zeolite may be subsequently treated by ion exchange and/or calcining as set out in the '189 patent.

In another aspect of the present invention, high surface area porous molecular sieve materials are prepared from layered transition metal non-oxide chalcogenides. Layered transition metal non-oxide chalcogenides are treated with an organic cationic species or organic compound capable of forming a cationic species which is exchanged into the material in order to increase the interlayer distance so as to permit the subsequent introduction of a polymeric chalcogenide precursor between the layers which can be converted to a polymeric chalcogenide bound to adjacent layers in order to form a more thermally stable layered material. The preparation of these materials may be preferably carried out in an inert environment such as argon or nitrogen gas. The layered transition metal non-oxide chalcogenides are of particular interest in that they may contain transition metal atoms having partially filled d-orbitals, which may result in metal-to-metal bonding within the layers. Molecular sieve materials thus prepared are therefore believed to possess a unique catalytic chemistry.

Examples of layered transition metal chalcogenides are well-known in the art. Intercalation of these materials with alkali and alkaline earth metal ions is taught in Schollhorn, R.; Meyer, H., *Mat. Res. Bull.* 1974, 9, 1237, incorporated herein by reference. This reference also sets out the structural scheme of such materials. Organoammonium ions can also occupy the interlayer regions of these materials as taught in Schollhorn, R.; Zagefka, H.; Butz, T.; Lerf, A., *Mat. Res. Bull.* 1979, 14, 369 and Schollhorn, R.; Sick, E.; Lerf, A. *Mat. Res. Bull.* 1975, 10, 1005, both of which are incorporated herein by reference.

The layered transition metal chalcogenides include layered metal dichalcogenides of the empirical formula $MX_2$ where X is selected from the group consisting of S, Se and Te and M is a transition metal selected from Groups IVA, IVB, VA, VIA, VIIA and VIIIA of the Periodic Chart. Preferably M is selected from the group consisting of Ti, Zr, Hf (Group IVA); Sn, Pb (Group IVB); V, Nb, Ta (Group VA); Mo, W (Group VIA); Tc, Re (Group VIIA) and Pt (Group VIIIA). M may be in octahedral coordination and/or trigonal prismatic coordination with the X atoms. $TiS_2$ is layered material particularly well-suited to the present invention.

These layered meta dichalcogenide materials are generally electrically. However, they can be reduced, for example, by contact with an aqueous alkali metal salt which acts as a reducing agent, e.g. in the case of $MS_2$ materials, $Na_2S_2O_4$. Other reducing agents can include alkali metal salts of borohydride or See e.g. Schollhorn, R. Sick, E; and Left, A.; *Mat. Res. Bull,* Vol. 10, page 1005. (1975). The reduction of the material results in the formation of a negative charge layer which becomes balanced by the presence of the alkali metal ion between the layers. Subsequent treatment with agents, particularly if they are cationic, can be enhanced by this reduction treatment. However, of a neutral swelling agent can occur with $MX_2$ materials even in the absence of such reduction. Indeed, the amount of swelling agent, e.g. n-alkylamine incorporated into the layered material can be dependent nature of the metal atom in the layer, i.e., the electronic band structure of the layered material. This can also the amount of polymeric chalcogenide precursor, e.g. polymeric oxide precursor such as tetraethylorthosilicate may later be sorbed between the layers.

Layered metal $MX_2$ pillared by the method of the present invention, particularly those where X is sulfur are believed suitable for use in petroleum processing, particularly in the removal of heteroatoms from residual chargestocks.

The method of the present invention may also be used to prepare thermally stable layered materials containing interspathic polymeric chalcogenides where the layered material is a perovskite-related layered oxide. Perovskite-related layered oxides are known in the art and are described, for example by Dion, M; Ganne, M., Tournoux, M; in *Mat. Res. Bull,* 981, 16, 1429. These materials as well as their organic-swelled analogues, e.g., those which are octylamine-swelled, are disclosed in U.S. Pat. No. 4,593,013. Such materials can be treated by the method of the present invention to incorporate interspathic polymeric chalcogenides therein. Both of these references are incorporated herein by reference. See also, Structure Properties and Preparation of Perovskite Type Compounds by F. Galasso, Pergamon Press, 1969, and Jacobson et al, *Inorg. Chem,* 1985, 24, 3727, both of which are incorporated herein by reference.

The perovskite-related layered-oxides used herein may be represented by the formula $M_m[A_{n-1}B_nO_{3n+1}]$ wherein M is a charge-balancing interspathic cation. $[A_{n-1}B_nO_{3n+1}]$ represents a perovskite-like layer wherein A is one more metal atoms capable of occupying 12-coordinate sites, B is a metal atom capable of occupying 6-coordinate sites, m is greater than 0, preferably less than or equal to 1 and n is greater than or equal to 2, preferably 3 is less than or equal to n is less than or equal to 7. Each layer comprises a cubic arrangement of corner-shared $BO_6$ octahedral with A occupying a 12-coordinated site in the center of each cube. For purposes of the present invention, the term "cubic arrangement" can include any generally cubic or pseudo-cubic arrangement.

The thickness of each layer in terms of $BO_6$ octahedra is denoted by n. In other words, the layers can vary, for example, between 3 and 7 $BO_6$ octahedra in thickness, depending on the perovskite-like layered material. Perovskite-like layered materials treated by the method of the present invention preferably have layers of a low charge density in order to exhibit the ion exchange properties necessary for incorporation of the more common propping agents prior to intercalation with polymeric chalcogenide precursor. Although some perovskite-like layered materials have a charge density per formula unit of two or more, the perovskite-like layered materials treated by the present invention preferably have a charge density of one or less. However, it is possible that a propping agent of requisite shape and charge can exchange with the interspathic cations in materials where m is greater than 1.

During preparation of the perovskite-related layered oxide according to the method of the present invention it has been found beneficial to carry out the swelling step utilizing a cationic species or cationic species precursor at temperatures above ambient, say, e.g. 70° to 110° C., say about 100° C. Similarly, the interspathic polymeric chalcogenide precursor is preferably introduced to the layered oxide at temperatures above ambient, e.g. 70° to 100° C., say about 80° to 90° C. The products thus prepared can be described as a thermally stable composition comprising a perovskite-related layered oxide containing an interspathic polymeric oxide of an element selected from Groups IB, IIB, IIIA, IIIB, IVA, IVB, VA, VB, VIA, VIIA and VIIIA of the Periodic Table, preferably an element selected from Group IVB of the Periodic Table, e.g., interspathic polymeric silica. One such composition is comprised of perovskite-like layers represented by the formula $Ca_2Nb_3O_{10}$ containing an interspathic polymeric oxide such as interspathic polymeric silica.

M can be a monovalent, divalent or trivalent cation, preferably a monovalent cation selected from the group consisting of Li, Na, K, Rb, Cs, $NH_4$ and H, while A can be one or more mono-, di- or trivalent cations selected from the group consisting of Groups IA, IIA and IIIB and the lanthanides and B can be one or more transition metals selected from Re and Groups IVB, VB and VIB. In one preferred embodiment, $A_{n-1}$ can be $Ca_2Na_{n-3}$ and B is Nb; in other words, the perovskite layer is represented by the formula $Ca_2Na_{n-3}Nb_nO_{3n+1}$. Preferably in such cases, M is K and n is 3, e.g., $KCa_2Nb_3O_{10}$.

The method of the present invention ma also be used in treating layered titanometallates of the general formula $A_x(M_{x/n}Ti_{2-x/n})O_4$ where x ranges from greater than about 0 to less than about 2, where n=1 and M is a trivalent cation or x ranges from greater than about 0 to less than about 4 where n=2 and M is a divalent cation. Preferably x ranges from about 0.6 to about 0.9. A is a monovalent cation e.g., a large alkali metal cation selected from the group consisting of Cs, Rb and K, M is a divalent or trivalent metal cation selected, for example, from the group consisting of Mg, Sc, Mn, Fe, Cr, Ni, Cu, Zn, In, Ga and Al and n is 1 for trivalent M or 2 for divalent M. For example, M can be both In and Ga. Structurally, these mixed metal oxides consist of layers of $(M_xTi_{1-x})O_6$ octahedra which are trans edge-shared in one dimension and cis edge-shared in the second dimension forming double octahedral layers which are separated by the A cations in the third dimension. These materials can be prepared by high temperature fusion of a mixture of (1) metal oxide, (2) alkali metal carbonate or nitrate and (3) titanium dioxide; or by fusion of a mixture of alkali metallate and titanium dioxide. Such fusion can be carried out in air at temperatures ranging between 850° to 1100° C. The layered titanometallates can be prepared by thoroughly grinding the reagents to homogeneous mixtures and firing in ceramic crucibles. The resulting powders are ground to about 20 to 250 mesh, preferably about 100 mesh, prior to the organic swelling and polymeric oxide intercalation steps. The ground titanometallate layered material is then treated with a "propping agent" as described earlier, for example aqueous alkylammonium halide, say, octylammonium chloride. It has been found necessary to maintain a low hydrogen ion concentration to prevent decomposition of the titanometallate structure as well as to prevent preferential sorption of hydrogen ion over the propping agent. A pH range of 6 to 10, preferably 7 to 8.5 is generally employed during treatment with the propping agent. After this treatment, it has been found advantageous to wash out excess propping agent using a propping agent-soluble reagent followed by washing with water prior to treatment with the polymeric chalcogenide precursor. For example, ethanol is soluble in and hence suitable for use with the oft-employed n-octylamine propping agent. Such washing permits greater incorporation of the polymeric oxide precursor by the layered titanometallate while the water treatment allows penetration of water into the interlayer treatment which will assist in hydrolyzing the polymeric oxide precursor.

The "propped" layered titanometallate is thereafter treated with a compound capable of forming polymeric oxide upon hydrolysis or other polymerizing reactions, such as those compounds described above. Weight uptakes of 20 to 25 weight percent have been observed during such treating. The treated layered material is then exposed to suitable conversion conditions, as discussed earlier, to form the layered titanometallate material of the present invention.

The resulting products exhibit thermal stability at temperatures of 500° C. or even higher as well as substantial sorption capacities (as much as 10 to 15 wt % for $H_2O$ and $C_6$ hydrocarbon). Silica-pillared titanometallates possess interlayer separations of greater than 12A and surface areas greater than 250 $m^2/g$ when divalent metal atoms, e.g., Mg, Ni, Cu and Zn, are present as the metal M of the titanometallate. Silica-pillared titanometallates incorporating trivalent metal atoms, e.g., Sc, Mn, Fe, Cr, In, Ga and Al can possess interlayer separations of 6 to 15 A. The calcined products of the present invention, particularly titanometallates containing interspathic polymeric oxides as prepared by the method of the present invention are suited to use as catalysts for petroleum processing owing to their high surface areas, large interlayer openings, thermal stability and the wide variety of metal atoms which may be incorporated therein.

Further description of the layered titanometallate starting materials and their methods of preparation can be found in the following references, all of which are incorporated herein by reference:

Reid, A. F.; Mumme, W. G.; Wadsley, A. D. *Acta Cryst.* (1968), B24, 1228; Groult, D.; Mercy, C.; Raveau, B. *J. Solid State Chem.* 1980, 32 289; England, W. A.; Burkett, J. E.; Goodenough; J. B., Wiseman, P. J. *J. Solid State Chem.* 1983, 49 300.

Use of these layered titanometallates as the layered metal chalcogenide of the present invention permits inclusion of different metal atoms into the layered chalcogenide material being treated which allows potential catalytically active sites to be incorporated in the stable chalcogenide layer itself. Moreover, variable amounts of metal atoms may be added to provide a catalyst with optimum activity for a particular process. Furthermore, the infinite trans-edge shared layer structure of the titanometallates instead of the sheared 3-block structure of $Na_2Ti_3O_7$ may reduce or eliminate shearing of the layers as a possible mechanism for thermal decomposition of the calcined intercalated material. These titanometallate materials may possess even greater thermal stability than silicotitanate molecular sieves. In addition, the variable charge density on the oxide layer possible for these layered titanometallate materials, due to the various oxidation states of the incorporated metal atom and the varying stoichiometry of the layered titanometallate, can determine the amount of the organic compound capable of forming a cationic species, e.g., which can be exchanged into the material. Thus, the amount of polymeric chalcogenide, e.g., polymeric silica, that is incorporated into the calcined material is also variable which, in turn, permits variance of the ultimate concentration of the polymeric oxide pillars between the layers of the final product.

Figure 2:
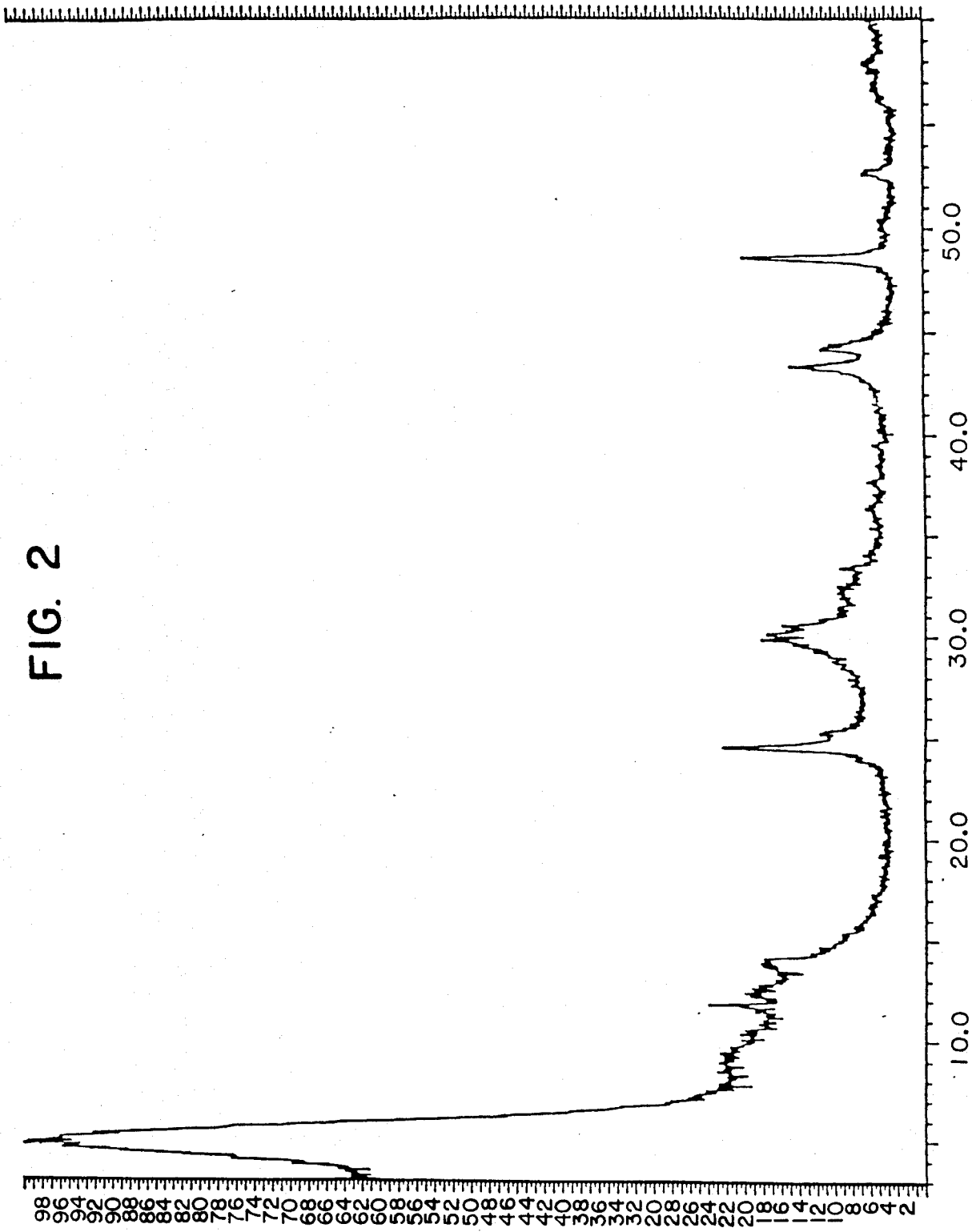
Figure 3:
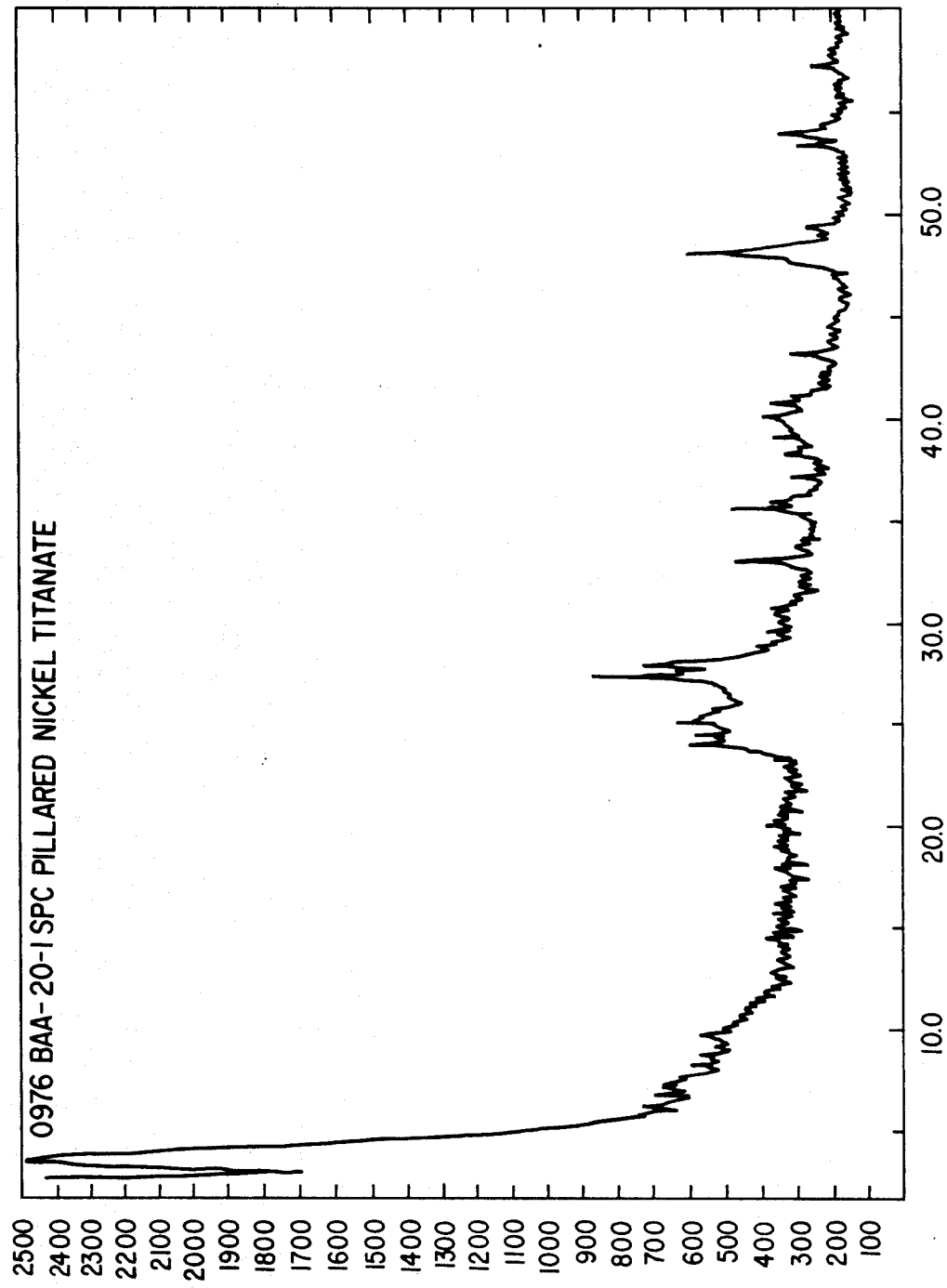

The present invention is illustrated further by the following examples and the accompanying drawings which provide X-ray diffraction patterns of the silicotitanates of Example 4 (FIG. 1) and Example 9 (FIG. 2) as well as that of the titanometallate of Example 66 (FIG. 3).

In these examples, adsorption data were determined as follows: A weighed sample was contacted with the desired pure adsorbate vapor at a pressure less than the vapor-liquid equilibrium pressure of the adsorbate at room temperature. Adsorption was complete when a constant pressure in the adsorption chamber was reached (overnight for water, 3 hours for hydrocarbons); e.g., 12 mm of mercury for water and 40 mm for n-hexane and cyclohexane. Samples were then removed and weighed. The increase in weight was calculated as the adsorption capacity of the samples. Nitrogen BET surface areas were reported in $m^2/g$. X-ray diffraction data was obtained by standard techniques using K-alpha doublet of copper radiation.

When alpha value is examined, it is noted that the alpha value is an approximate indication of the catalytic cracking activity of the catalyst compared to a standard catalyst and it gives the relative rate constant (rate of normal hexane conversion per volume of catalyst per unit time). It is based on the activity of the highly active silica alumina cracking catalyst taken as an alpha of 1 (Rate Constant =0.16 sec$^{-1}$). The alpha test is described in U.S. Pat. No. 3,354,078 and in *The Journal of Catalysis*, Vol. IV. pp. 522-529 (August 1965).

EXAMPLE 1

Calcination of $Na_2Ti_3O_7$

A 20 g sample of $Na_2Ti_3O_7$ (Alpha Products, Lot #101380) was calcined in air at 1000° F. for 1 hour. The product exhibited the following physical properties:

| Surface Area: | 5.0 m$^2$/g |
|---|---|
| Sorption (g/100 g): | |
| $H_2O$ | 0.3 |
| Cyclohexane | 0.4 |
| n-Hexane | 0.2 |

Thus, the starting titanate has low surface area and negligible hydrocarbon sorptive capacity. The X-ray diffraction pattern of $Na_2Ti_3O_7$ indicates a layer thickness of less than 8.4 angstroms.

EXAMPLE 2

Ion Exchange of Sodium Trititanate with Octylammonium Ion 300 g of concentrated HCl (36.6%) was dissolved in 700 g of water, and the resulting solution was placed in a 2 liter beaker, stirred with a magnetic stirrer, and cooled in ice. n-Octylamine ($C_8H_{17}NH_2$, 410 g) was then added portionwise at a rate such that the solution temperature remained below 45° C. Sodium titanate (100 g of $Na_2Ti_3O_7$) was added, and the mixture was transferred to a 2 liter polypropylene jar and heated at 100° C. for 24 hours with occasional stirring. The product was filtered, washed with 3 liters of hot water and then 250 ml of absolute ethanol (room temperature), and finally liters of hot water.

The dried product (230° F., 1 hour) had the following composition (mole ratios):

$1.00TiO_2:0.16C_8H_{17}NH_2:0.077Na_2O$

EXAMPLE 3

Addition of Polymeric Oxide Precursor

The product of Example 2 (15.0 g) was stirred in 100 g tetraethylorthosilicate in a 250 ml beaker covered with a watch glass for 3 days at room temperature. The product was filtered and dried at room temperature for 17 hours.

EXAMPLE 4

Calcination of Product from Example 3

The product of Example 3 (15.0 g) was calcined in air for 3 hours in an oven pre-heated to 538° C. (1000° F.). The novel silicotitanate product has the x-ray diffraction pattern shown in FIG. 1 and listed in Table 2 as well as the following composition (mole ratios):

$1.00TiO_2:0.69SiO_2:0.068Na_2O$

The product had a surface area of 289 m$^2$/g and exhibits the following sorption characteristics (g/100 g):

| $H_2O$ | 9.8 |
|---|---|
| Cyclohexane | 8.8 |
| n-Hexane | 5.8 |

These data indicate that interspathic incorporation of polymeric silica can dramatically increase surface area and sorptive behavior of the layered titanate. The product had an alpha-value of 4.

TABLE 2

TABULATION OF THE PRINCIPAL PEAKS IN THE X-RAY POWDER DIFFRACTION PATTERN OF THE PRODUCT OF EXAMPLE 4

| Line Number | Degrees 2 Theta | d(A) | $I/I_{max}$ (Relative Intensity) |
|---|---|---|---|
| 1 | 4.96 | 17.81 | 100 |
| 2 (Broad) | 12.19 | 7.26 | 15 |
| 3 (Broad) | 13.88 | 6.38 | 12 |
| 4 | 24.52 | 3.63 | 78 |
| 5 (Shoulder) | 25.05 | 3.56 | 24 |
| 6 | 30.07 | 2.972 | 31 |
| 7 | 33.37 | 2.685 | 7 |
| 8 | 43.30 | 2.090 | 28 |
| 9 | 44.28 | 2.046 | 16 |
| 10 | 48.53 | 1.876 | 73 |
| 11 | 52.74 | 1.736 | 8 |

EXAMPLE 5

Calcination of Layered Titanate Containing Only Organic Ammonium

The product of Example 2 (10 g) was calcined in air at 1000° F. for 3 hours. The product has a surface area of 10 m$^2$/g and the following sorption characteristics (g/100 g):

| $H_2O$ | 0.6 |
|---|---|
| Cyclohexane | 0.7 |
| n-Hexane | 0.9 |

Thus, tetraethylorthosilicate treatment of the product from Example 2 is necessary for producing a material of high surface area and sorptive capacity.

EXAMPLE 6

Direct Addition of Polymeric Oxide Precursor to Sodium Trititanate

A mixture of 15.0 g $Na_2Ti_3O_7$ in 100 g tetraethylorthosilicate was stirred for 3 days at room temperature. The mixture was filtered and air dried for 24 hours at room temperature. The product had the following composition (mole ratios):

$1.00TiO_2:0.012SiO_2:0.33Na_2O$

The absence of significant levels of silica in this product indicate the necessity of pre-exchange with organic ammonium ions for silica-incorporation.

A portion of this product (7.0 g) was calcined at 1000° F. in a pre-heated oven for 3 hours. The product had the following properties:

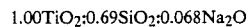

| Surface Area | 5.0 m$^2$/g |
|---|---|
| Sorption (g/100 g): | |
| $H_2O$ | 0.2 |
| Cyclohexane | 0.3 |
| n-Hexane | 0.2 |

19

Thus, the absence of significant silica-incorporation produces a product with low surface area and negligible sorption capacity.

EXAMPLE 7

Repeat Preparation—Ion Exchange of Octylammonium in Sodium Trititanate 320.8 g of concentrated HCl (36.6%) were dissolved in 700 g water and stirred in a 2 liter beaker. The mixture was cooled in ice and 427.1 g n-octylamine was added portionwise at such a rate to keep the solution temperature below 50° C. After addition of the amine, 100 g $Na_2Ti_3O_7$ was added, and the resulting mixture was transferred to a 2 liter polypropylene jar and heated with occasional stirring at 100° C. for 24 hours. The product was filtered, and washed sequentially with 3 liters of hot water, 250 ml absolute ethanol (room temperature), and 2 liters of hot water. The dried product (121° C. (250° F.)for 1 hour), had the following composition (mole ratios):

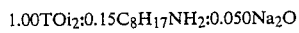

$1.00 TiO_2 : 0.15 C_8H_{17}NH_2 : 0.050 Na_2O$

EXAMPLE 8

Repeat Preparation—Addition of Polymeric Oxide Precursor

The product of Example 7 (75 g) was stirred with 500 g tetraethylorthosilicate in a one liter beaker covered with a watch glass for 3 days at room temperature. The product was filtered and dried at room temperature for 24 hours.

EXAMPLE 9

Repeat Preparation—Calcination of Product from Example 8

The product of Example 8 (64.g) was calcined in air for 3 hours at 1000° F. (pre-heated oven). The novel silicotitanate product had an x-ray diffraction pattern (FIG. 2) similar to that observed for the product of Example 4 and has the following composition (mole ratios):

$1.00 TiO_2 : 0.23 SiO_2 : 0.053 Na_2O$

The product has a surface area of 191 m²/g and exhibits the following sorption characteristics (g/100 g):

| $H_2O$ | 9.5 |
| cyclohexane | 6.6 |
| n-hexane | 5.1 |

The product had an alpha-value of 3.

EXAMPLE 10

Repeat Preparation of Thermally Stable Layered Titanate

Comprising Interspathic Silica Using n-Octylamine

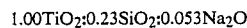

Concentrated HCl (320.8 g of 36.6% HCl) was dissolved in 700 g water, and the resulting solution was stirred and cooled in an ice bath. n-Octylamine (427.1 g) was added portionwise, keeping the solution below 50° C. 100 Grams of $Na_2Ti_3O_7$ was added, and the mixture was transferred to a 2 liter polypropylene jar and heated at 100° C. with occasional stirring for 24 hours. Approximately one-half of the mixture was filtered, washed sequentially with 1.5 liters hot water, 125 ml absolute ethanol, and 1 liter hot water, and dried at room temperature for 24 hours.

15 Grams of this product was stirred in 100 g tetraethylorthosilicate at room temperature for 72 hours. The product was filtered, air-dried for 1 hour at room temperature, and calcined in air for 3 hours at 538° C. (1000° F.) in a pre-heated oven. The product had an x-ray diffraction pattern similar to those of Examples 4 and 9, except that the lowest angle peak was observed at 4.4° (2 theta) corresponding to a d-spacing of 20.1 A. The product had the following composition (mole ratio) and properties:

| 1.00 $TiO_2$ : 0.41 $SiO_2$ : 0.051 $Na_2O$ | |
|---|---|
| Surface Area (m²/g) | 275 |
| Sorption (g/100 g) | |
| $H_2O$ | 12.9 |
| Cyclohexane | 9.3 |
| h-hexane | 7.1 |

EXAMPLE 11

Preparation of Thermally Stable Layered Titanate Comprising Interspathic Silica Using n-Heptylamine The following illustrates the use of n-heptylamine as swelling agent for the preparation of a silicotitanate molecular sieve: 78.9 g of 37.2% HCl was dissolved in 176 g water. The mixture was stirred and cooled in an ice bath while 95.4 g n-heptylamine was added portionwise at such a rate to keep the solution temperature below 40° C. 25 Grams of $Na_2Ti_3O_7$ were added, and the resulting mixture was heated at 100° C. in a polypropylene jar for 24 hours with occasional stirring. The mixture was filtered, washed with 1 liter hot water, and air-dried for 24 hours at room temperature.

A portion of this dried product (15 g) was stirred in 100 g of tetraethylorthosilicate as previously described at room temperature for 72 hours. The product was filtered, air-dried for 24 hours at room temperature, and calcined in air for 3 hours at 538° C. (1000° F.) in a preheated oven.

The product has an x-ray diffraction pattern similar to those of Examples 4, 9, and 10, except that the lowest angle peak was observed at 4.0° (2 theta) or 22.1 angstroms d-spacing. The product had the following composition (mole ratios) and properties:

| 1.00 $TiO_2$ : 0.55 $SiO_2$ : 0.11 $Na_2O$ | |
|---|---|
| Surface Area (m²/g) | 241.0 |
| Sorption (g/100 g) | |
| $H_2O$ | 10.9 |
| Cyclohexane | 4.5 |
| n-hexane | 5.1 |

EXAMPLE 12

Preparation of Thermally Stable Layered Titanate Comprising Interspathic Silica Using n-Dodecylamine The following illustrates the use of n-dodecylamine as swelling agent for the preparation of a silicotitanate molecular sieve: To a solution of 236.6 g of 37.2% HCl in 525 g of water were added 459.4 g n-dodecylamine. The mixture was transferred to a 2 liter polypropylene jar and heated at 100° C. for 3 hours to obtain a homogeneous mixture. 75 Grams of $Na_2Ti_3O_7$ were added, and the resulting mixture was heated at 100° C. for 24 hours. The hot mixture was then diluted with 1 liter of hot water and allowed to filter overnight to dryness at room temperature. The product was re-slurried with 1 liter hot water, filtered, washed with 4 liters of hot water, and air-dried at room temperature for 24 hours.

30 Grams of the dried product was stirred in 200 g tetraethylorthosilicate in a beaker covered with a watch glass at room temperature for 66 hours. The product was filtered, dried at room temperature for 24 hours, and calcined in air for 5 hours at 538° C. (1000° F.) in a pre-heated oven.

The product had an x-ray diffraction pattern similar to those of Examples 4, 9, 10, and 11, except that the lowest angle peak was observed at 3.0° (2 theta) or 29.4 angstroms d-spacing. The product had the following composition (mole ratios) and properties:

| 1.00 $TiO_2$:0.79 $SiO_2$:0.047 $Na_2O$ | |
|---|---|
| Surface Area ($m^2/g$) | 461 |
| Sorption (g/100 g) | |
| $H_2O$ | 19.0 |
| Cyclohexane | 15.8 |
| n-hexane | 13.5 |

EXAMPLE 13

Preparation of Thermally Stable Layered Titanate From Hydrogen Exchanged Trititanate - Octylamine Method Acid titanate, $H_2Ti_3O_7$, was prepared from exchange of Na in $Na_2Ti_3O_7$ with 1M HCl in triplicate as described below: 780.7 g of 37.4% HCl was diluted to 8 liters total volume with water in a 12 liter 4-necked round bottom flask equipped with a mechanical stirrer, reflux condenser, and thermometer. 500 Grams of $Na_2Ti_3O_7$ were added, and the resulting mixture was heated with stirring at 75°-80° C. for 24 hours. The solution was then filtered and washed with 2 liters of hot water. The procedure was repeated in triplicate. After the third exchange, the product was washed with hot water until chloride free. The product after drying in vacuo at 77° C. had an x-ray diffraction pattern similar to that reported for $H_2Ti_3O_7$ by H. Izawa, S. Kikkaw, and M. Kolzumi, *J. Phys. Chem.*, 86,5023 (1982).

The acid titanate was then swollen with n-octylamine as follows: 50 g n-octylamine was dissolved in 150 g of water in a 500 ml round-bottom flask equipped with a magnetic stirrer and reflux condenser. 10 Grams of $H_2Ti_3O_7$ were added, and the resulting mixture was refluxed with stirring for 24 hours. The solid product was filtered, washed with 750 ml hot water, and air-dried at room temperature for 24 hours.

Eight grams of this dried product were stirred in 53 g tetraethylorthosilicate in a beaker loosely covered with plastic for 67 hours at room temperature. The product was filtered, dried at room temperature for 24 hours, and calcined in air for 3 hours at 538° C. (1000° F.) in a pre-heated oven.

The final product had an x-ray diffraction pattern similar to those of Examples 4, 9, 10, 11, and 12 with the lowest angle peak observed at 5.0° (2 theta) or 17.9 angstroms d-spacing. The silicotitanate product of this Example had the following composition (mole ratios) and properties:

| 1.00 $TiO_2$:0.19 $SiO_2$:0.0067 $Na_2O$ | |
|---|---|
| Surface Area ($m_2/g$) | 276 |
| Sorption (g/100 g) | |
| $H_2O$ | 11.5 |
| Cyclohexane | 8.2 |
| n-hexane | 8.2 |

EXAMPLE 14

Preparation of Thermally Stable Layered Titanate from Hydrogen Exchanged Trititanate - Hexylamine Method The acid titanate described in Example 13 was swollen with n-hexylamine as follows: 39.1 g n-hexylamine were added to 150 g water in a 500 ml round-bottom flask equipped with a magnetic stirrer and reflux condenser. 10 Grams of $H_2Ti_3O_7$ were added and the resulting mixture was refluxed with stirring for 24 hours. The solid product was filtered, washed with 750 ml hot water, and air dried at room temperature for 24 hours.

Eight grams of this dried product were stirred in 53 g tetraethylorthosilicate in a beaker loosely covered with plastic for 72 hours at room temperature. The product was filtered, dried at room temperature for 24 hours, and calcined in air for 3 hours at 538° C. (1000° F.) in a pre-heated oven.

The final product had an X-ray diffraction pattern similar to those of Examples 4, 9, 10, 11, 12 and 13 with the lowest angle peak observed at 5.2° (2 theta) or 17.0 angstroms. The silicotitanate product of this Example had the following composition (mole ratios) and properties:

| 1.00 $TiO_2$:0.22 $SiO_2$:0.0062 $Na_2O$ | |
|---|---|
| Surface Area ($m_2/g$) | 201 |
| Sorption (g/100 g) | |
| $H_2O$ | 8.8 |
| Cyclohexane | 5.7 |
| n-hexane | 5.5 |

EXAMPLE 15

Preparation of Thermally Stable Layered Titanate from Hydrogen Exchanged Trititanate - Propylamine Method The acid titanate described in Example 13 was swollen with n-propylamine as follows: 22.9 g n-propylamine was dissolved in 150 g water in a 500 ml round-bottom flask equipped with a magnetic stirrer and reflux condenser. 10 Grams of $H_2Ti_3O_7$ were added and the resulting mixture was refluxed with stirring for 24 hours. The solid product was filtered, washed with 750 ml hot water, and air dried for 24 hours at room temperature.

Eight grams of this dried product were stirred in 53 g of tetraethylorthosilicate in a beaker loosely covered with plastic for 72 hours at room temperature. The product was filtered, dried at room temperature for 24 hours, and calcined in air for 3 hours at 538° C. (1000° F.) in a pre-heated oven.

The final product had an X-ray diffraction pattern similar to those of Examples 4, 9, 10, 11, 12, and 13 with the lowest angle peak observed at 8.7° (2 theta) or 10.2 angstroms d-spacing. The silicotitanate product of this Example had the following composition (mole ratios) and properties:

| 1.00 $TiO_2$:0.21 $SiO_2$:0.0068 $Na_2O$ | |
|---|---|
| Surface Area ($m_2/g$) | 48 |
| Sorption (g/100 g) | |
| $H_2O$ | 3.0 |
| Cyclohexane | 2.2 |
| n-hexane | 1.8 |

EXAMPLE 16

Preparation of TEABr-Exchanged Magadiite

A 5 g natural magadiite sample from Trinity County, Calif. was dried 3 hours at 110° C. in air. The X-ray diffraction pattern of the dried sample showed a low angle peak at 5.6° (2 theta) indicating a basal spacing of 15.8 A. The surface area was 28 $m^2/g$ by nitrogen adsorption method. Other adsorption properties were 13% $H_2O$, 1.5% $CyC_6$ and 1.0% n-$C_6$. The alpha activity of the sample was 0.3. The sample was then exchanged twice with 10 ml/g of 0.1N tetraethylammonium bromide at ambient temperature for 24 hours, filtered, water-washed and dried at 110° C. for 3 hours. The surface area of the sample was 39 $m^2/g$ indicating very little intercalation. The TEABr exchanged magadiite was thereafter calcined at 260° C. for 2 hours. The x-ray pattern was similar to the dried unexchanged magadiite with basal spacing of 15.8 A. The surface area of the sample was 36 $m^2/g$.

EXAMPLE 17

Preparation of ($Al_2(OH)Cl_5$)-Exchanged Magadiite

Five grams of natural magadiite from Trinity County, Calif. were added to 82 ml of water and 18 ml of dilute $Al_2(OH)Cl_5$ solution with traces of silicate. The mixture was aged at room temperature for one hour with stirring. The solution was then heated to boiling for one hour and the solution pH adjusted to the 4.8–5.0 with 0.1N $NH_4OH$. The sample was filtered, hot-water washed twice and dried. The surface area of the sample was 129 $m^2/g$.

EXAMPLE 18

Preparation of H-Magadiite

Twenty grams of natural magadiite were sized to pass through a 25 mesh size screen and added to 100 ml of $H_2O$. The mixture was adjusted to a pH of about 2 and held there by addition of 0.1N HCl within a 24 hour period. A total of 435 ml of 0.1N HCl was used. The sample was filtered, water-washed and dried. The x-ray pattern of the sample showed a peak at 7.8° (2 theta) evincing an 11.3 A d-spacing indicating the structure was in a collapsed state. The calcined sample (3 hours at 538° C. in air) had the same d-spacing. The adsorption properties were 27 $m^2/g$ surface area, 0.8% $H_2O$, 1.2% $CyC_6$ and 2.0% n-$C_6$.

EXAMPLE 19

Preparation of Octylamine-Containing Magadiite

Five grams of the acid treated and dried magadiite from Example 18 were reacted with 10 g of dimethylsulfoxide and 6 g of octylamine for 24 hours at room temperature. The product was air-dried after decanting off excess liquid. The X-ray pattern exhibited a low angle (2 theta) peak at 2.7° indicating a basal or d-spacing of 32.7 A. The air calcined (540° C.) sample had a basal or d-spacing of 11.2 A, indicating the removal of the organic propping agent.

EXAMPLE 20

Preparation of Magadiite Intercalated with Polymeric Silica

One part of the uncalcined magadiite from Example 19 was treated with 8 parts of tetraethylorthosilicate for 24 hours at ambient temperature. The product was filtered, dried and calcined in air at 538° C. for 2 hours. The X-ray pattern of the calcined product had a low angle (2 theta) peak at 4.6° relating to a basal or d-spacing of 19.2 A. The adsorptive properties were: surface area 391 $m^2/g$, $H_2O$ 13.1%, $CyC_6$ 10.9% and n-$C_6$ 10.6%. The alpha activity of the sample was 0.4.

EXAMPLE 21

Preparation of Magadiite Intercalated with Polymeric Silica in the Presence of Acid One part of the uncalcined magadiite from Example 19 was treated with 8 parts of tetraethylorthosilicate and 0.4 parts of 0.1N HCl with the same procedure described in Example 20. The lowest theta (2 theta) x-ray diffraction peak was 3.1° and basal or d-spacing 28.5 Angstroms. The surface area of the sample after calcination was 505 $m^2/g$. Other adsorptive properties were: $H_2O$ 18.6%, $CyC_6$ 15.5% and n-$C_6$ 14.8%. The alpha activity of the sample was found to be 0.7. These properties indicate that a thermally stable and porous magadiite has been prepared.

A comparison of reaction protocol and product properties of Examples 19 to 21 is set out in Table 3.

TABLE 3

| The Properties of Intercalated Magadiite | | | |
|---|---|---|---|
| | Ex. 19 | Ex. 20 | Ex. 21 |
| Base Material | Natural Magadiite from California | | |
| Acid Treatment | None | 0.1 NHCl added to get 2 pH | |
| Intercalation | None | DMSO + Octylamine + TEOS | DMSO + Octylamine + TEOS + HCl |
| Calcination | 540° C. in air for 2 hours | | |
| Basal Spacing, A | 11.1 | 19.2 | 28.5 |
| ° (2 theta of Low Angle) | 8 | 4.6 | 3.1 |
| Product Properties | | | |
| Surface Area, $m^2/g$ | 30 | 391 | 565 |
| $H_2O$ Adsorption, % | 13 | 13.1 | 18.6 |
| $CyC_6$ Adsorption % | 1.5 | 10.9 | 15.5 |
| $nC_6$ Adsorption % | 1.0 | 10.6 | 14.8 |
| Alpha-Activity | 0.3 | 0.5 | 0.7 |

EXAMPLE 22

Preparation of Synthetic Magadiite Containing Interspathic Titanium Sulfide

A 20 g. sample of the propped product of Example 40a is reacted first with hydrogen sulfide in order to introduce $H_2S$ into the interlayer and then with a 100 g sample of titanium tetraisopropoxide. The titanium tetraisopropoxide reaction is conducted at room temperature for 3 days in a sealed polypropylene bottle, whereafter the resultant slurry is filtered, air-dried and calcined for 2 hours at 538° C. (1000° F.) in air. The product is a magadiite pillared with titanium disulfide.

EXAMPLE 23

Preparation of Synthetic Makatite 60.0 g tetraethylammonium bromide were dissolved in a solution containing 1.6 g $H_3BO_3$, 8.0 g NaOH and 100 g $H_2O$. This solution was added to 58.0 g of colloidal silica (30%) and thoroughly mixed. The mixture was crystallized in a polypropylene jar at 100° C. for 127 days. The crystalline product was water washed, dried at 118° C. and submitted for X-ray analysis which showed the presence of makatite type material and trace unidentified crystalline material.

The product was analyzed and yielded the following results:

| Product composition | |
|---|---|
| B (weight percent) | 0.03 |
| N (weight percent) | 0.03 |
| Na (weight percent) | 11.2 |
| $Al_2O_3$ (ppm) (weight percent) | 450 |
| $SiO_2$ (weight percent) | 62.0 |
| Ash (weight percent) | 77.0 |

A portion of the product was calcined at 500° C. Adsorption properties of the calcined material is set out below:

| | |
|---|---|
| Cyclohexane (weight percent) | 0.2 |
| n-Hexane (weight percent) | 0.1 |
| $H_2O$ (weight percent) | 0.3 |
| Surface Area, $m^2/g$ | 13 |

EXAMPLE 24

Preparation of Synthetic Makatite 73.0 g of 40% tetraethylammonium hydroxide solution were added to a solution containing 10.0 g NaOH, 25 ml 2,2',2''-nitrilotriethanol (TEA) and 60.0 g $H_2O$. This solution was added to a mixture of 54.0 g HiSil silica plus 25.0 ml TEA and thoroughly mixed to form a mixture of following composition:

| | |
|---|---|
| $SiO_2/Al_2O_3$ = | infinity |
| $OH/SiO_2$ = | 0.57 |
| $R/SiO_2$* = | 0.25 |
| $H_2O/SiO_2$ = | 7.4 |
| Triethanolamine/$SiO_2$ = | 0.48 |

*R = Tetraethylammonium

The mixture was crystallized in a polypropylene jar at 100° C. for 141 days. The washed and dried crystalline product was submitted for X-ray analysis which showed the sample contained mainly makatite, with some unidentified crystalline material.

Analysis of the product was carried out and gave the following results:

| Composition (weight percent) | |
|---|---|
| N | 0.59 |
| Na | 8.6 |
| $Al_2O_3$ | 0.45 |
| $SiO_2$ | 70.5 |
| Ash | 83.9 |

A sample of the product, calcined at 500° C. had the adsorption properties set out below:

| | |
|---|---|
| Cyclohexane (weight percent) | 2.0 |
| n-Hexane (weight percent) | 1.8 |
| $H_2O$ | 3.2 |
| Surface Area, $m^2/g$ | 11 |

EXAMPLE 25

Preparation of Synthetic Kenyaite

A sample of synthetic kenyaite was prepared in a manner similar to that reported by K. Beneke and G. Lagaly in *American Mineralologist*, Vol. 68, p. 818 (1983), incorporated herein by reference. A mixture of 10.22 g 87.2% KOH and 57.4 g of amorphous precipitated silica (HiSil 233) in 300 g water was crystallized in a 600 ml autoclave with stirring at 150° C. for 3 days. The product was filtered, washed with 4 liters water, and dried at 250° F. for one hour. The dried product had the following composition:

| | |
|---|---|
| 4.0% | K |
| 0.39% | $Al_2O_3$ |
| 68.0% | $SiO_2$ |
| 73.55% | Ash |

A sample calcined in air for one hour at 1000° F. had low surface area.

EXAMPLE 26

Preparation of Synthetic Makatite Containing Interspathic Polymeric Silicon Oxide Five parts of sample from Example 23 was added to 20 parts of water. Dilute HCl (0.1N) was added to lower the pH of the mixture to 2 and to hold at that level for at least 16 hours. The sample was filtered, washed and dried. A mixture of 15 parts of $H_2O$ and 7.5 parts of n-octylamine was then added to the dried and acid-treated sample and reacted for 16 hours. The sample was filtered and dried at room temperature for another 3 hours. The air-dried sample was transferred into 15 parts of tetraethylorthosilicate (TEOS) for about 20 hours at room temperature. The X-ray diffraction pattern of the dried, TEOS-treated sample indicated good crystallinity and a low angle peak at 2 theta of 3.9° corresponding to a spacing of 22.7 Angstroms. The sample after calcination at 538° C. in air for 3 hours did not have a distinctive x-ray pattern but showed the following surface and adsorptive properties which demonstrated excellent porosity, superior to that of the unpillared and calcined base:

| | |
|---|---|
| Surface Area ($m^2/g$) | 722 |
| Adsorption (percent by weight) | |
| $H_2O$ | 25.6 |
| $nC_6$ | 18.9 |
| $CyC_6$ | 19.0 |

EXAMPLE 27

Preparation of Synthetic Makatite Containing Interspathic Polymeric Silicon Oxide The sample from Example 24 was treated by the procedure described in Example 26, except the pH level of the acid-treating step was kept at 4. The properties of the pillared and calcined sample were as follows:

| Surface area (m²/g) | 488 |
|---|---|
| Adsorption (percent by weight) | |
| H₂O | 17.0 |
| nC₆ | 15.0 |
| CyC₆ | 16.0 |

The x-ray pattern of the pillared sample had a low angle peak at two theta of 3.4° before calcination. After calcination, the pattern shows a mainly amorphous material, except for a minute peak at 22.5° at two theta which may indicate a trace of zeolite beta.

The alpha activity of the activated sample was 24.

EXAMPLE 28

Preparation of Synthetic Kenyaite Containing Interspathic Polymeric Oxide

A 40 g sample from Example 25 was added to 100 g of water. Hydrochloric acid (0.1N) was added to adjust the pH of the mixture to a pH of 2 and held at that level for at least 24 hours. The solids recovered by filtration were water-washed and vacuum-dried and were then added to a mixture of 80 g H₂O and 40 g n-octylamine at room temperature and reacted for 24 hours. The sample was again filtered and dried in air. One part of the air dried sample was treated with 3 parts of tetraethylorthosilicate for 24 hours at ambient conditions.

The recovered solid had an x-ray pattern with a low angle peak at 2.5° (2 theta) indicating a d-spacing of 35.2 angstroms. The surface area and sorptive properties of the calcined (1000° F.) sample are set out below and indicate that the sample had been pillared and converted into a highly porous material.

| Surface Area (m²/g) | 596 |
|---|---|
| Adsorption (% wt) | |
| H₂O | 17.5 |
| nC₆ | 17.8 |
| Cy₆ | 20.9 |

EXAMPLE 29

Intercalation of Layered Clay (Bentonite) With Polymeric Silica 20 g of Volclay-type bentonite was combined with 200 g of water. The pH of the mixture was adjusted to and maintained at about 2 over 24 hours at room temperature by the intermittent addition of 0.1N HCL (145cc). The resulting acid-exchanged clay was washed with water, dried at room temperature, added to a mixture of 50 g DMSO and 30 g n-octylamine and reacted at room temperature for 24 hours whereupon it was filtered and dried. 100 g of tetraethylorthosilicate were then added and the treatment at room temperature lasted for about 24 hours. The resulting product was calcined in air at 540° C. for 3 hours. X-ray diffraction showed a broad low angle peak at about 3.5° (2 theta). The corresponding basal spacing was about 25.2 A. Surface area increased from 30 to about 324 m²/g. Water sorption increased from 1.0 to 10.7 wt. %, cyclohexane sorption increased from 0.5 to 10.9 wt. % and n-hexane increased from 0.8 to 8.9 wt %.

EXAMPLE 30

Preparation of Layered Titanate Comprising Interspathic Zeolite

Concentrated HCl (320.8 g of 36.6% HCl) is dissolved in 700 g water, and the resulting solution is stirred and cooled in an ice bath. n-Octylamine (427.1 g) is added portionwise, keeping the solution below 50° C. 100 Grams of Na₂Ti₃O₇ is added, and the mixture was transferred to a 2 liter polypropylene jar and heated at 100° C. with occasional stirring for 24 hours. Approximately one-half of the mixture is filtered, washed sequentially with 1.5 liters hot water, 125 ml absolute ethanol, and 1 liter hot water, and is dried at room temperature for 24 hours.

15 Grams of this product are stirred in a mixture of 100 g tetraethylorthosilicate at room temperature for 72 hours, filtered, and then air-dried at room temperature for 24 hours. The product is treated hydrothermally with 0.5 g sodium aluminate at elevated temperature for 72 hours. The product is filtered, air-dried for 1 hour at room temperature, and calcined in air for 3 hours at 538° C. (1000° F.) in a pre-heated oven. The resulting product is a layered titanate comprising interspathic ZSM-5.

EXAMPLE 31

Preparation of Thermally Stable Layered Titanate from Hydrogen Exchanged Trititanate With Sequential Propping The acid titanate described in Example 13 is swollen with n-propylamine as follows: 22.9 g n-propylamine is dissolved in 150 g water in a 500 ml round-bottom flask equipped with a magnetic stirrer and reflux condenser. 10 Grams of H₂Ti₃O₇ are added and the resulting mixture is refluxed with stirring for 24 hours. The solid product is filtered, washed with 750 ml hot water, and air dried for 24 hours at room temperature.

The n-propylamine-containing titanate is then swollen with n-octylamine as follows: 50 g of n-Octylamine are dissolved in 150 g of water in a 500 ml round-bottom flask equipped with a magnetic stirrer and reflux resulting mixture is refluxed with stirring for 24 hours. The solid product is filtered, washed with 750 ml hot water, and air-dried at room temperature for 24 hours.

Eight grams of this dried product are stirred in 53 g tetraethylorthosilicate for 67 hours at room temperature. The product is filtered, dried at room temperature for 24 hours, and calcined in air for 3 hours at 538° C. (1000° F.) in a pre-heated oven.

The final product has an X-ray diffraction pattern similar to those of Examples 4, 9, 10, 11, 12 and 13 with the lowest angle peak being observed at 5.0° (2 theta) or 17.9 angstroms d-spacing.

EXAMPLES 32–35

Divalent Ion-Exchange of Pillared Silicotitanate

A solution of 500 g Na₂Ti₃O₇ was refluxed with stirring in a solution of 427 g n-octylamine, 313 g 37.5% HCl and 7,000 g water for 22 hours in a 4-necked, round bottom flask equipped with a thermometer, reflux condenser, mechanical stirrer, and a stopper. The solution was decanted, reslurried with 2 liters hot water and decanted again. An additional 2 liters of hot water were added and the resulting mixture was filtered and dried at room temperature for 24 hours. About 500 g of this product were slurried in 500 cc of absolute ethanol, filtered, and dried for one hour in air at room temperature. This product was reslurried in one liter water and heated with occasional stirring at 100° C. for 16 hours. The product was thereafter filtered and dried at room temperature for 24 hours.

400 g of dried product were mechanically stirred in 3000 g tetraethylorthosilicate in a 10 liter beaker covered with perforated aluminum foil for 72 hours at room temperature. The resulting material was filtered and air-dried at room temperature for 24 hours. A 200 g portion of this product was calcined in nitrogen for 2 hours at 510° C. (950° F.) followed by calcining in air for one hour at 510° C. (950° F.). The silicotitanate product had a surface area of 273 m$^2$/g and the following composition (wt. %):

|  |  |
|---|---|
| TiO$_2$ | 68.7 |
| SiO$_2$ | 24.8 |
| Na | 2.3 |

The material had an alpha value of 2. After hydrothermal treatment (100% steam, 2 hours, 538° C.), the product had a surface area of 43 m$^2$/g.

The product was then exchanged once with stirring with excess (9.8 moles metal salt/mole Na) 0.12M solutions of each of the following metal salts at room temperature for 24 hours: Ni(NO$_3$)$_2$.6H$_2$O; Cu(NO$_3$)$_2$.2½H$_2$O, Co(NO$_3$)$_2$.6H$_2$O, Zn(NO$_3$)$_2$.6H$_2$O. After exchange, solutions were filtered, water washed, dried at 121° C. (250° F.) for 2 hours and calcined at 427° C. (800° F.) in air for one hour. Analyses were:

| Ex. | Surface Area (m$^2$/g) | % Ni | % Cu | % Zn | % Co | % Na | % SiO$_2$ | % TiO$_2$ |
|---|---|---|---|---|---|---|---|---|
| 32 | 252 | 1.4 | — | — | — | 1.1 | 23.7 | 71.1 |
| 33 | 241 | — | 2.2 | — | — | 1.1 | 23.2 | 73.4 |
| 34 | 245 | — | — | 2.0 | — | 0.97 | 23.5 | 70.1 |
| 35 | 254 | — | — | — | 1.8 | 1.0 | 23.4 | 71.7 |

All exhibited high surface area after exchange of about half of the original sodium in the silicotitanate with divalent ions. Each sample was then steamed at 538° C. (1000° F.) for 2 hours (100% steam) with the following results:

| Example | Surface Area (m$^2$/g) After Steaming |
|---|---|
| 32 | 90 |
| 33 | 48 |
| 34 | 93 |
| 35 | 86 |

These results indicate improved hydrothermal stability as a result of Ni, Cu, Zn, or Co exchange.

EXAMPLE 36

Cesium Ion-Exchange of Pillared Silicotitanate

A mixture of 500 g Na$_2$Ti$_3$O$_7$, 427 g n-octylamine, 309.7, 37.8% HCl and 7000 g water was refluxed for 22 hours as previously described. The solution was decanted and filtered and dried on the filter at room temperature overnight. This product was then treated twice with absolute ethanol and water as follows: the solid product was reslurried in 2 liters ethanol, filtered, and air-dried 6 hours at room temperature. This material was then slurried in 1.5 liters water, heated at 100° C. in a 2 liter polypropylene jar for 17 hours, filtered and dried at room temperature for 24 hours.

450 g of the dried product were mechanically stirred in 3000 g of tetraethylorthosilicate in a 10 liter beaker covered with perforated aluminum foil for 68 hours at room temperature and then filtered and dried in air at room temperature for about 4 days. This material was calcined in nitrogen at 510° C. (950° F.) for 2 hours and then in air for one hour at 510° C. (950° F.). The silicotitanate product had a surface area of 405 m$^2$/g and the following composition (wt. %):

|  |  |
|---|---|
| TiO$_2$ | 51.7 |
| SiO$_2$ | 39.9 |
| Na | 1.8 |
| Ash | 98.1 |

This material had an alpha-value of 3. After hydrothermal treatment (100% steam, 2 hours, 538° C.), the product had a surface area of 62 m$^2$/g.

Three grams of the resulting silicotitanate were added to 125 ml of 0.1N CsCl solution. The mixture was stirred in a polypropylene bottle at ambient temperature for 7 days. The solid was separated by filtration and was then water-washed to chloride free and dried in vacuo. The exchanged sample was analyzed and found to contain 0.82% Na and 4.35% Cs by wt. About half of the original sodium was exchanged by the cesium ions.

EXAMPLES 37 and 38

Trivalent Ion-Exchange of Pillared Silicotitanate

Further samples of the silicotitanate produced in Example 36 were exchanged four times with stirring with excess (4.6 moles metal salt/mole Na) 0.10M solutions of the following salts: Al(NO$_3$)$_3$.9H$_2$O and La(NO$_3$)$_3$.6H$_2$O. Samples were filtered and water-washed after each exchange; after the final exchange, both samples were calcined in air at 510° C. (850° F.). Surface areas and chemical analyses were:

| Ex. | Surface Area (m$^2$/g) | % Al | % La | % Na | % SiO$_2$ | % TiO$_2$ |
|---|---|---|---|---|---|---|
| 37 | 355 | 0.49 | — | 0.77 | 42.1 | 55.9 |
| 38 | 374 | — | 2.05 | 0.70 | 42.5 | 56.2 |

Slightly more than half of the original sodium was exchanged by the trivalent ions, and high surface area was retained. The product of Example 37 had an alpha-value of 6, indicating considerable activation as a result of exchange of Na by Al. Each example was steamed (100% steam, 2 hours 1000° F.) with the following results:

| Example | Surface Area (m$^2$/g) After Steaming |
|---|---|
| 37 | 262 |
| 38 | 198 |

Thus, trivalent ion exchange dramatically improved hydrothermal stability.

EXAMPLE 39

Tetravalent Ion-Exchange of Pillared Silicotitanate

This example demonstrates exchange of sodium in a silicotitanate with a tetravalent ion (ceric ion). The silicotitanate product in Example 36 was exchanged once with stirring with excess (9.9 moles metal salt per Na) 0.1M Ce(SO$_4$)$_2$·2H$_2$SO$_4$ at room temperature for 24 hours. The solution was filtered, water-washed, dried at 121° C. (250° F.), and calcined at 427° C. (800° F.) in air for one hour. The product had a surface area of 378 m$^2$/g and the following composition (wt. %):

| | |
|---|---|
| TiO$_2$ | 43.0 |
| SiO$_2$ | 37.6 |
| Na | 0.74 |
| Ce | 1.9 |

EXAMPLE 40

Preparation of Synthetic Magadiite Containing Interspathic Polymeric Silicon Oxides and Aluminum Oxides (a) A gel was produced by mixing 400 g Cabosil silica in 54.4 g 98% NaOH and 1.4 kg water. The gel was crystallized in a 2 liter polypropylene jar at 100° C. for 23 days to produce synthetic magadiite, which was then filtered, washed with hot water and dried at (250° F.) overnight. The dried product had the following composition (wt %):

| | |
|---|---|
| SiO$_2$ | 83.3 |
| Na$_2$O | 6.9 |
| Al$_2$O$_3$ | 0.01 |

100 g of the dried product were added to 600 ml of distilled water, titrated with 0.1N HCl to a pH of 2, and held at a pH of 2 for 24 hours. The product, after being filtered, washed with 8 liters of distilled water, and air dried on the filter, had 95 ppm Na.

The resultant product (80 g) was treated for 24 hours with a solution of 80 g of octylamine in 160 g of DMSO, filtered, air dried and then held for subsequent treatments.

(b) A solution of tetraethylorthosilicate (TEOS) and aluminum isopropoxide (AIP) was prepared as follows:

80 g of aluminum isopropoxide (30–35%) in isobutanol (Alfa) were placed in a 250 ml polypropylene bottle and heated in a steam chest at 100° C. for 16 hours. 51.0 g TEOS (Baker, practical grade) were added and this solution was stirred for 3 days at room temperature.

20 g of the octylamine propped product of (a) above were reacted with the TEOS/AIP solution for 3 days in a polypropylene bottle which was tightly sealed. The slurry was filtered, air dried, and calcined for 2 hours at 510° C. (950° F.) in air. The final product had an alpha=5 and the following composition (wt. %):

| | |
|---|---|
| SiO$_2$ | 72.90 |
| Al$_2$O$_3$ | 16.8 |

EXAMPLES 41–42

Preparation of Synthetic Magadiite Containing Interspathic Titanium Oxide and Silicon Oxide Further 20 g samples of the propped product of Example 40a were reacted respectively with 100 g samples of titanium tetraisopropoxide (Example 41) and tetraethylorthosilicate (Example 42). Each reaction was conducted at room temperature for 3 days in a sealed polypropylene bottle, whereafter the resultant slurry was filtered, air-dried and calcined for 2 hours at 538° C. (1000° F.) in air. The products had the following properties:

| | Composition (wt %) | | | |
|---|---|---|---|---|
| Example | Alpha | SiO$_2$ | Al$_2$O$_3$ | Ti |
| 41 | 3 | 53.7 | 0.015 | 27 |
| 42 | 1 | 94 | 0.0025 | — |

EXAMPLE 43

Preparation of Synthetic Magadiite Containing Interspathic Oxides of Aluminum and Silicon (a) 110 g of the acid form of synthetic magadiite prepared in a manner analogous to Example 40 were treated with a solution of 150 g of octylamine in 300 g of distilled water for 24 hours at room temperature. The slurry was filtered to a wetcake, reslurried (285 g of wetcake in 5.7 liters of distilled water), left for approximately 1 hour at room temperature, and refiltered. The product was composed of 238 g of paste-like material (41.54% solids).

(b) 294.2 g of aluminum isopropoxide (30–35%) in isobutanol were placed in a polypropylene bottle in a steam chest (100° C.) overnight. 171.6 g of solution was recovered after overnight heating. 220 g of tetraethylorthosilicate were added to the aluminum isopropoxide solution and the mixture was magnetically stirred for 9 days at room temperature.

(c) The product (b) was added to the product (a) then an additional 400 g of fresh tetraethylorthosilicate were added. This mixture was reacted for 65 hours at room temperature in a sealed polypropylene bottle with magnetic stirring. The slurry was filtered with difficulty, air dried, dried overnight at 110° C. and then calcined at 538° C. for 1 hour in flowing nitrogen followed by 2 hours in flowing air. The final product had an alpha=10 and the following composition (wt %):

| | |
|---|---|
| SiO$_2$ | 83.1 |
| Al$_2$O$_3$ | 8.7 |

EXAMPLE 44

Preparation of Synthetic Magadiite Containing Interspathic Oxides of Aluminum and Silicon 150 g of a high silica synthetic magadiite was acid exchanged with a solution of 0.5N HCl at a pH of 2.0 for 24 hours, filtered, washed chloride-free and air dried. The dried sample was treated with an aqueous n-octylamine solution 160 g (1.24 mol) of n-octylamine in 3,500 g (194.4 mol) of distilled water for 24 hours at room temperature, filtered, washed and air dried. A solution of 19 g of aluminum isopropoxide (0.093 mol) in 747 g of tetraethylorthosilicate (3.6 mol) was heated in a steam chest overnight. Thereafter, 120 g (61.45% solids) of the octylammonium form of the magadiite were stirred into the solution for 24 hours. The mixture was thereafter filtered, air dried and calcined for three hours at 538° C. in air. The resulting product was a synthetic magadiite pillared with a polymeric oxide of silicon and aluminum.

The surface area and sorption properties of the calcined magadiites obtained in Examples 40-44 are summarized below:

| Example | Surface Area m²/g | Sorption Capacity | | |
|---|---|---|---|---|
| | | $H_2O$ (12 Torr) | Cy—$C_6$ (40 Torr) | n-$C_6$ (40 Torr) |
| 40 | 289 | 14.2 | 8.2 | 4.7 |
| 41 | 158 | 9.2 | 4.4 | 3.3 |
| 42 | 307 | 7.2 | 6.0 | 4.3 |
| 43 | 450 | 16.3 | 12.3 | 10.9 |
| 44 | 504 | 19.1 | 15.1 | 13.7 |

EXAMPLES 45-49

Preparation of Synthetic Magadiite Co-Crystallized with Aluminum and/or Fe and Intercalated with Silica

EXAMPLE 45

24.5 g of dibenzyldimethylammonium chloride were added to a solution containing 0.63 g sodium aluminate (43.3% $Al_2O_3$, 32.2% $Na_2O$, 25.6% $H_2O$), 4.0 g NaOH and 30.0 g $H_2O$. The mixture was added to 134.0 g colloidal $SiO_2$ (30%) and thoroughly mixed. The mixture was heated at 140° C. in a static reactor for 21 days. X-ray analysis indicated a synthetic magadiite material containing trace amounts of mordenite.

EXAMPLE 46

2.49 g of $FeNH_4(SO_4)_2.12H_2O$ were dissolved in 11.0 g of $H_2O$. This mixture was added to a solution of 5.23 g NaOH dissolved in 11.0 g $H_2O$. The resulting mixture was added to 72.6 g of a 40% $SiO_2$ colloidal silica solution and thoroughly mixed and then crystallized in a static reactor at 150° C. for 21 days. X-ray analysis indicated a synthetic magadiite material.

EXAMPLE 47

A solution containing 5.16 g of $FeNH_4(SO_4)_2$ in 10.0 g $H_2O$ was mixed with a second solution containing 6.86 g dibenzyldimethylammonium chloride, 6.86 g NaOH and 25.0 g $H_2O$. The mixture was added to 136 g of 30% colloidal silica solution and thoroughly mixed. The reaction mixture was crystallized at 150° C. for 23 days. X-ray analysis indicated a synthetic magadiite material containing trace amounts of zeolite beta.

EXAMPLE 48

The following solutions were prepared:

| A. | $NaAlO_2$, | 1.5 g |
|---|---|---|
| | Benzyltriethylammonium chloride | 64.5 g |
| | $H_2O$ | 180.0 g |
| B. | NaCl | 22.2 g |
| | $H_2O$ | 345.0 g |
| C. | Q-Brand sodium silicate | |
| | (28.8% $SiO_2$, 8.9% $Na_2O$) | 156.0 g |
| | $H_2O$ | 510.0 g |
| D. | HCl (conc.) | 8.5 g |
| | $H_2O$ | 200.0 g |

A was added to B.
AB was added to C.
D was added to ABC and mixed well.

The reaction mixture was crystallized in a stirred reactor at 150° C. for 7 days. X-ray analysis indicated a synthetic magadiite material.

EXAMPLE 49

The following reagents were prepared:

| A. | $NaAlO_2$, g | 0.96 g |
|---|---|---|
| | NaOH | 2.8 g |
| | $H_2O$ | 13.60 g |
| B. | Benzyltributylammonium chloride | 22.3 g |
| C. | Colloidal silica (30%) | |

B was dissolved in A and mixed with C. The mixture was crystallized in a static reactor at 100° C. for 215 days. X-ray analysis indicated a synthetic magadiite material.

The compositions and properties of the layered products of Examples 45 to 49 are set out below in Table 4.

TABLE 4
Compositions and Properties of As-Synthesized Layered Silicates

| Example | 45 | 46 | 47 | 48 | 49 |
|---|---|---|---|---|---|
| Composition, wt % | | | | | |
| $SiO_2$ | 84.7 | 78.0 | 80.0 | 79.6 | 79.6 |
| $Al_2O_3$ | 0.73 | 0.18 | 0.05 | 2.1 | 2.0 |
| Fe | — | 0.83 | 1.1 | — | — |
| Na | 3.6 | 4.2 | 3.4 | 3.7 | 3.9 |
| N | 0.26 | — | 0.25 | 0.07 | 0.07 |
| Ash | 88.7 | 85.6 | 87.0 | 89.5 | 88.1 |
| $SiO_2/Al_2O_3$ | 200 | 750 | 2600 | 64.4 | 67.7 |
| Surface Area, m²/g | 56 | 5 | 95 | | |
| Sorption Properties | | | | | |
| Cyclohexane, wt % | 2.1 | 0.5 | 3.9 | | |
| n-Hexane | 2.2 | — | | | |
| $H_2O$ | 7.7 | 2.9 | 10.4 | | |

These materials were then intercalated by the following procedure:

Twenty-five parts by weight of each solid sample were added to one hundred parts of $H_2O$. The pH of each slurry was gradually adjusted to 2 by adding 0.1N HCl solution at room temperature and kept at a pH of 2 for 24 hours. Each solid was filtered and water washed and dried. To each dried sample, a mixture of 20 parts dimethylsulfoxide and 10 parts of n-octylamine was added and reacted for about 24 hours. Each mixture was filtered and dried on the filter for 3 hours. Each sample was then added to 100 parts of tetraethylorthosilicate at room temperature. The samples were filtered after a contact time of 24 hours. After drying, the samples were calcined at 1000° F. in air for 3 hours. Analysis of each product indicated a crystalline porous material. The compositions and properties of the resulting products are set out in Table 5 below.

TABLE 5

| Base Material | Properties of Pillared Silicates | | | | |
|---|---|---|---|---|---|
| | Ex. 45 | Ex. 46 | Ex. 47 | Ex. 48 | Ex. 49 |
| Surface Area, m²/g | 486 | 598 | 583 | 360 | 634 |
| Sorption Capacity, % | | | | | |
| $H_2O$ | 17.9 | 22.6 | 23.1 | — | — |
| $CyC_6$ | 14.8 | 19.8 | 19.1 | 10.9 | — |
| $N-C_6$ | 12.6 | 18.3 | 19.2 | — | — |
| Basal d-Spacing, Å | 24.0 | 24.5 | 25.9 | 25.2 / 17.7 | 30.5 |
| | 48 (mordenite contaminant) | 0.5 | 2.0 | 1.0 (zeolite beta contaminant) | 0.6 |

EXAMPLE 50
Preparation of Synthetic Magadiite Co-Crystallized with Aluminum and Intercalated with Polymeric Silica 16.7 Grams of dibenzyldimethylammonium chloride were dissolved in a solution containing 0.42 grams of sodium aluminate (43.3% $Al_2O_3$, 32.2% $Na_2O$, 25.6% $H_2O$), 4.0 g NaOH and 20.0 g $H_2O$. The mixture was then added to 90.0 g of colloidal silica (30%) and thoroughly mixed. The mixture was heated at 140° C. for 21 days in a static reactor at 118° C.

The resulting material was identified as a co-crystallized synthetic magadiite and had the following composition:

| | |
|---|---|
| N, Wt % | 0.28 |
| Na | 3.6 |
| $Al_2O_3$ | 0.75 |
| $SiO_2$ | 81.0 |
| Ash | 83.49 |
| $SiO_2/Al_2O_3$ molar ratio | 184 |

A portion of the material after being calcined for 16 hours at 540° C. had the following properties:
Cyclohexane adsorption, 40 torr = 1.3 g/100 g
Surface area of calcined material = 29 m²/g 15 Grams of the uncalcined dried (118° C.) product were contacted with 20 cc of 10% $NH_4Cl$ solution per gram of material at 85° C. with stirring for five one hour contacts. The Na level was reduced to below 0.01%. The washed product was dried at 118° C., calcined for 3 hours at 540° C. in air and had an alpha value of 28.

Five grams of the dried, uncalcined material was added to 40 ml of $H_2O$. 0.1N HCl was added dropwise to obtain and maintain the solution at 2 pH for 24 hours. The mixture was filtered, water-washed and dried in air for 24 hours. The dried sample was then treated with a solution mixture of 10 g of dimethylsulfoxide and 5 g of octylamine for 24 hours at ambient temperature. The sample was again filtered and air dried on the filter for 3 hours. The x-ray diffraction pattern of the dried sample had a main low angle peak at 3.4° 2 theta indicating a basal spacing of 25.9 angstroms.

The resulting material was added to 20 g of tetraethylorthosilicate for 24 hours. The sample was filtered, dried at 110° C. for 3 hours and calcined at 540° C. for 3 hours in air. The x-ray diffraction pattern of the calcined sample showed a 3.8° (2 theta) low angle peak indicating a basal spacing of 23.2 Å. The adsorptive properties were: surface area 415 m²/g, $H_2O$ adsorption at 12 torr, 14.2%, cyclohexane at 40 torr, 10.9% and n-hexane at 40 torr, 9.4%. Two grams of the calcined example were slugged and sized to 14 to 25 mesh material. The sample was then tested for cracking catalytic activity by the alpha test. An alpha value of 14 was obtained indicating a very catalytically active material.

EXAMPLE 51
Preparation of Synthetic Kenyaite Co-Crystall With Aluminum and Intercalated With Polymeric Silica Aluminum-tri-sec-butoxide (14.1 g) was dissolved in $H_2O$ (150 g) and stirred overnight (approximately 18 hrs). The solution was slowly added to colloidal silica gel (172 g, Ludox LS, 30% $SiO_2$). To this mixture KOH (10 g), which had been dissolved in $H_2O$ (50 g), was slowly added. 5 g of a pure silica kenyaite was added to seed the reaction. The reaction mixture was aged in a steambox for 2 hrs and the resulting gel mixture was crystallized at 150° C. for 120 hrs while stirring under autogenous pressure. The product was filtered, washed with distilled $H_2O$, and air-dried for characterization. X-ray diffraction indicated a kenyaite product. The surface area was 34 m²/g and chemical analysis indicated a $SiO_2/Al_2O_3$ of about 25. 40 Grams of the resulting material were suspended in 400 ml of $H_2O$. To this slurry, 1N HCl was added until the pH equalled 2. The stirring of the suspension was continued for 24 hrs whereafter the suspension was filtered, washed, and air-dried. The product (7 g) was resuspended in 20 g of $H_2O$ and octylamine (20 g) was added to the resulting suspension. This was stirred approximately 18 hrs, heated for approximately 1 hr, filtered, washed with warm $H_2O$, air-dried for 24 hrs and then dried in a vacuum oven at 160° F. for 3 hrs. The dried product was slurried in tetraethylorthosilicate (TEOS) (35 g) in a closed polypropylene jar for 72 hrs. The material was filtered, air-dried, and calcined at 500° C. for 4 hrs. The final product had an x-ray low-angle diffraction line at 38.4 Å.

EXAMPLE 52
Preparation of Synthetic Kenyaite Co-Crystallized With Aluminum and Intercalated With Polymeric Silica $Al(NO_3)_3 \cdot 9H_2O$ (6.42 g) was dissolved in $H_2O$ (100 g) and slowly added to colloidal silica (200 g, Ludox LS, 30% $SiO_2$). To this mixture KOH (12 g) which had been dissolved in $H_2O$ (100 g), was added. The mixture was aged in a steambox for ½ hour and the resulting gel was dispersed in a blender. The gel was charged to an autoclave and crystallized at 150° C. for 120 hrs while stirring under autogenous pressure. The product was filtered, washed with distilled $H_2O$, and air-dried. X-ray diffraction pattern indicated a kenyaite product. 40 Grams of the resulting product which had a $SiO_2/Al_2O_3$ molar ratio of about 100 were suspended in 400 mls of $H_2O$. To this slurry, 1N HCl was added until the pH was about 2. The suspension continued to stir for 24 hrs., was filtered, washed, and air-dried. The product (7 g) was resuspended in 20 g of H$_2$O and octylamine (20 g) was added to the resulting suspension. This was stirred approximately 18 hrs, heated for approximately 1 hr, filtered, washed with warm H$_2$O, air-dried for 24 hrs., then dried in a vacuum oven at 160° F. for 3 hrs. The dried product was slurried in tetraethylorthosilicate (TEOS) (35 g) in a closed polypropylene jar for 72 hrs. The material was filtered, air-dried, and calcined at 500° C. for 4 hrs. The final product had an x-ray low-angle diffraction line at 38.4 A.

EXAMPLE 53

Oligomerization of Propylene with Silicotitanate 5.0 Grams from that portion of the pillared silicotitanate material of Example 36 which was not hydrothermally treated and not cesium-exchanged were charged to a 450 cc autoclave. Approximately 150 cc liquid propylene were charged and the temperature adjusted to 150° C. The pressure quickly rose to 1040 psig. The reaction was allowed to continue for a total of 24 hours at a stirring rate of 1000 rpm. At the end of this time, unreacted propylene was vented from the autoclave and a total of 3.4 grams of liquid product were recovered. Gas chromatographic analysis of this liquid product showed it to have the following product distribution (wt %):

| COMPONENT | Wt % |
| --- | --- |
| C$_6$ | 25.2 |
| C$_9$ | 53.5 |
| C$_{12}$ | 16.7 |
| C$_{15}$ | 4.3 |
| C$_{18}$ | 0.3 |
| C$_{21}$+ | 0 |

EXAMPLE 54

Oligomerization of Propylene with Nikel-Exchanged Silicotitanate

A mixture of 500 g Na$_2$Ti$_3$O$_7$, 770 g n-octylamine, 559 g of 37.8% HCl and 5 liters of water was refluxed for 22 hours. The solution was cooled to 70° C. and 281 g of 37.8% HCl was added. The product was filtered, washed with 10 l of hot water and dried overnight at room temperature. The solid product was slurried in 3 liters of ethanol for one hour at room temperature, filtered and air dried 24 hours at room temperature. 900 Grams of this material were slurried in 4 liters of water and stirred at room temperature for 23 hours, filtered and dried at room temperature for 24 hours. 825 g of the dried product were mechanically stirred in 5.5 kg of tetraethylorthosilicate in a 10 liter beaker covered with perforated aluminum foil for 72 hours at room temperature and then filtered and dried in air at room temperature for about 24 hours. This material was calcined in nitrogen at 950° F. for 2 hours and then in air for one hour at 950° F. The silicotitanate product had a surface area of 299 m$^2$/g and the following composition (wt %):

| | |
| --- | --- |
| TiO$_2$ | 70.2 |
| SiO$_2$ | 21.7 |
| Na | 3.3 |
| Ash | 100.0 |

7.5 Grams of the pillared silicotitanate product were added to a 0.5M Ni(NO$_3$)$_2$ solution prepared by dissolving 72.5 g Ni(NO$_3$)$_2$.6H$_2$O in 500 ml de-ionized water in a 1 liter flask. The resulting solution was stirred at room temperature for about 68 hours. The catalyst was then filtered from the solution, washed with de-ionized water, and dried for one hour in an oven maintained at 100° C. The catalyst was then pelletized and sized to 14/25 mesh. The pelletized catalyst was then carefully calcined by heating from ambient temperature to 400° C. at the rate of 1.5° C./min, then held at 400° C. for 4 hours.

5.0 Grams of this catalyst was charged to a 300 cc autoclave. Approximately 150 ml liquid propylene were added. The temperature was adjusted to 150° C. Pressure in the autoclave rapidly increased to 1440 psig. The reaction was allowed to continue for a total of 24 hours. At this time, unreacted propylene was vented from the autoclave. Approximately 8.8 grams liquid product were recovered from the reactor. Gas chromatographic analysis of this material showed it to have the following composition:

| COMPONENT | Wt % |
| --- | --- |
| C$_6$ | 16.6 |
| C$_9$ | 56.7 |
| C$_{12}$ | 17.7 |
| C$_{15}$ | 6.7 |
| C$_{18}$ | 2.0 |
| C$_{21}$+ | 0.4 |

EXAMPLE 55

Oligomerization of Propylene Using NH$_4$+ and H+-Exchanged Silicotitanate

A 1.0M solution of NH$_4$NO$_3$ was prepared by dissolving 80 gms NH$_4$NO$_3$ in one liter de-ionized water in a 2 liter flask. 15 Grams of the pillared silicotitanate material of Example 36 which was not hydrothermally treated and not cesium-exchanged were added and the mixture stirred at room temperature for approximately 70 hours. The catalyst was filtered from the solution, washed thoroughly with de-ionized water and dried for one hour in an oven maintained at 100° C. 7 Grams of this catalyst were further treated by heating from ambient temperature to 250° C. at the rate of 1° C./min, then held at 250° C. for a total of four hours. 5.0 Grams of this catalyst were charged to a 300 cc autoclave. Approximately 150 cc liquid propylene were added and the temperature adjusted to 150° C. The pressure quickly rose to 1425 psig. The reaction was allowed to continue with stirring at 1000 rpm for a total of 22.5 hours. At the end of this period, unreacted propylene was vented from the autoclave and approximately 3.7 grams of liquid product were recovered. Gas chromatographic analysis of this material showed it to have the following composition

| COMPONENT | Wt % |
| --- | --- |
| C$_6$ | 22.1 |
| C$_9$ | 60.3 |
| C$_{12}$ | 14.1 |
| C$_{15}$ | 3.4 |

-continued

| COMPONENT | Wt % |
|---|---|
| $C_{18}$ | 0.1 |
| $C_{21}+$ | 0 |

Another 7 grams of this catalyst were calcined by heating from ambient temperature to 500° C. at 2° C./min, then held at this temperature for a total of 12 hours. 5 Grams of the resulting catalyst were charged to a 300 cc autoclave, 150 cc liquid propylene were added and the reaction temperature increased to 150° C. The pressure reached 1415 psig. The reaction was allowed to continue for a total of 24 hours under autogenous pressure at a stirring rate of 1000 rpm. At the end of this time, unreacted propylene was vented from the autoclave and a total of 4.6 grams of liquid product were recovered. GC analysis of this material showed it to have the following product distributions:

| COMPONENT | Wt % |
|---|---|
| $C_6$ | 15.4 |
| $C_9$ | 60.1 |
| $C_{12}$ | 18.6 |
| $C_{15}$ | 4.9 |
| $C_{18}$ | 1.1 |
| $C_{21}+$ | 0 |

EXAMPLE 56

Oligomerization of Propylene Using Aluminum-Exchanged Silicotitanate 300 g of the silicotitanate product of Example 54 (non-nickel-exchanged). This product had a surface area of 223 m²/g and the following composition (wt %):

| | |
|---|---|
| $TiO_2$ | 66.7 |
| $SiO_2$ | 23.6 |
| Na | 2.5 |
| $Al_2O_3$ | 0.65 |
| Ash | 97.96 |

5.0 Grams of this catalyst were loaded into a 300 cc autoclave. Approximately 150 cc of liquid propylene were added and the reaction temperature adjusted to 150° C. The pressure rose to 1415 psig. The reaction was allowed to continue with stirring at 1000 rpm for a total of 24 hours. At the end of this time, the unreacted propylene was vented from the reactor and a total of 14.5 gms liquid product were recovered. Gas chromatographic analysis of this material showed it to contain the following composition:

| COMPONENT | Wt % |
|---|---|
| $C_6$ | 13.3 |
| $C_9$ | 52.3 |
| $C_{12}$ | 24.4 |
| $C_{15}$ | 8.0 |
| $C_{18}$ | 2.0 |
| $C_{21}+$ | 0 |

EXAMPLE 57

Oligomerization of Propylene Using Low Alkali Metal Content Silicotitanates 1 kg of $Na_2Ti_3O_7$ was exchanged in triplicate with 16 liters of 1.0 M HCl with stirring at 170° F. for 24 hours in order to exchange out alkali metal ions. The solid was filtered and washed with 4 liters of water after the first two exchanges. After the third exchange, the product was filtered, washed chloride-free with water, and dried at 170° F. for 1 hour in vacuo. A mixture of 700 g of this material in 700 g n-octylamine and 10.5 liters water was refluxed with stirring for 23 hours. The product was filtered, washed with 10 liters of hot water, and dried at room temperature for 3 days. 600 g of this product were stirred in 4 kg tetraethylorthosilicate for 67 hours at room temperature, filtered and dried for 24 hours at room temperature. 800 Grams of the dried product were calcined in $N_2$ at 950° F. for 2 hours and in air for 1 hour at 950° F. The final silicotitanate product had a surface area of 394 M²/g and the following composition (wt %):

| | |
|---|---|
| $TiO_2$ | 65.2 |
| $SiO_2$ | 37.3 |
| Na | 0.34 |
| Ash | 97.61 |

5.0 Grams of the catalyst were charged to a 300 cc autoclave. Approximately 150 cc liquid propylene were charged and the temperature adjusted to 150° C. The pressure increased to 1375 psig. The reaction was allowed to continue with stirring at 1000 rpm for a total of 23.5 hours under autogenous pressure. At the end of this time, unreacted propylene was vented from the autoclave and approximately 69.3 grams liquid product were recovered. Gas chromatographic analysis of this material showed it to have the following composition (wt %):

| COMPONENT | Wt % |
|---|---|
| $C_6$ | 4.2 |
| $C_9$ | 48.7 |
| $C_{12}$ | 36.5 |
| $C_{15}$ | 10.5 |
| $C_{18}$ | 0.1 |
| $C_{21}+$ | 0 |

EXAMPLE 58

Oligomerization of Propylene Using Unpillared Nickel-Exchanged Sodium Trititanate (Comparative Example)

10 Grams of a dense form $Na_2Ti_3O_7$ (purchased from Alfa Products) were exchanged with $Ni(NO_3)_2.6H_2O$ using the same procedure described in Example 54. 5 Grams of the resulting catalyst were charged to a 300 cc autoclave, approximately 150 ml liquid propylene added and the temperature increased to 150° C. Initial pressure was 1500 psig. After 16 hours at these conditions, no pressure drop had been observed. At this point the reaction was terminated. This result demonstrates that pillaring is necessary for the catalytic activity of these catalysts.

EXAMPLE 59

Oligomerization of 1-Hexadecene Using Low Alkali Metal Content Silicotitanate

5 Grams of the catalyst prepared in Example 57 were charged to a 300 cc autoclave along with 75 grams of 1-hexadecene that had been percolated over alumina just prior to use. The autoclave was heated to 275° C. and the reaction allowed to continue in the liquid phase for a total of 68 hours with stirring at 950 rpm. At the end of this time, the reactor was opened and the products analyzed by gas chromatography. The recovered liquid was found to contain 18.7% (by weight) of the lube range dimer, $C_{32}$. The unreacted monomer was distilled from the dimer. The VI of this $C_{32}$ material was determined to be 138 with a kinematic viscosity of 4.5 cSt at 100° C.

EXAMPLE 60

Oligomerization of 1-Decene Using Low Alkal Metal Content Silicotitanate

5 Grams of the catalyst prepared in Example 57 were charged to a 300 cc autoclave along with 75 grams 1-decene that had been percolated over alumina just prior to use. The temperature in the autoclave was raised to 150° C. and the reaction allowed to continue under these conditions with stirring at 1000 rpm for a total of 28 hours. A sample of the liquid after this time showed conversion of 1-decene to be 26.1% (by weight). The observed oligomer selectivities were as follows: $C_{20}=88.1\%$, $C_{30}=10.5\%$, $C_{40}=1.4\%$. After this time, the temperature was increased to 200° C. and the reaction allowed to continue for an additional 118 hours at this temperature. At the end of this time, the reaction was terminated. Analysis of the liquid product showed conversion of 1-decene to be 65.5%. The selectivity to the various oligomers was as follows: $C_{20}=83.7\%$, $C_{30}=14.8\%$, $C_{40}=1.6\%$.

The liquid from this reaction was distilled to remove any unreacted 1-decene and a significant portion of the dimeric products. The resulting liquid product had the following product distribution: $C_{20}=27.2\%$, $C_{30}=62.3\%$, $C_{40}=10.4\%$. The V.I. of this material was measured to be 94.3 with a kinematic viscosity of 4.9 cSt at 100° C.

EXAMPLE 61

Oligomerization of 1-Hexadecene with Nickel-Exchanged Silicotitanate

5 Grams of the catalyst of Example 54 were charged to a 300 cc autoclave along with 75 grams of 1-hexadecene that had been percolated over activated alumina just prior to use. The temperature was increased to 275° C. and the reaction allowed to continue for 16 hours. Analysis of the liquid after this time showed conversion to be 14.7%. The temperature was raised to 325° C. and the reaction allowed to continue for an additional 100 hours. After this time, the reaction was terminated. Analysis of the liquid showed 14% conversion to the dimer, $C_{32}$. Unreacted monomer was then distilled from the $C_{32}$ product. The VI of the lube range material was determined to be 115 with a kinematic viscosity of 4.2 cSt at 100° C.

EXAMPLE 62

Preparation of a Silica-Pillared Chalcogenide* Molecular Sieve 10.0 g of the layered metal dichalcogenide $TiS_2$ are reduced by contacting with a 1M aqueous solution of $Na_2S_2O_4$. The reduced product and 11.5 g of n-octylamine, 8.4 g 37.1% HCl, and 100 g $H_2O$ are placed in a Pyrex tube which is evacuated and sealed. The tube is heated to 100° C. for 4 days. The contents of the tube are filtered and air dried. This product is stirred in $O_2$-free $H_2O$ for 1 day, then filtered and dried under a flow of $N_2$. The solid thus obtained is then treated with tetraethylorthosilicate (5 g TEOS/g solid) for 72 hours. After filtering and drying in $N_2$, the solid is calcined in $N_2$ at 500° C. for 4 hours. The resulting material exhibits increased n-hexane and water sorption and increased surface area over the $TiS_2$ starting material.

EXAMPLE 63

Preparation of Perovskite-Related Layered Oxide $Ca_2Nb_3O_{10}$ Containing Interspathic Polymeric Silica $KCa_2Nb_3O_{10}$ was prepared by reacting a thoroughly ground mixture of 200 g $K_2CO_3$, 69.04 g $CaCO_3$ and 398.36 g $Nb_2O_5$ in a mole ratio of 1:4:3 at 750° C. in air for 6 hours followed by 24 hours of heating at 1149° C. The material was cooled, reground and refired at 1149° C. for 24 hours. 100 g of $KCa_2Nb_3O_{10}$ were then stirred in 300 ml of 6MHCl for 24 hours at 60° C. The resulting solid was cooled, filtered, washed with water and dried overnight resulting in hydrated $HCa_2Nb_3O_{10}$. 30 Grams of this material were stirred in 200 ml of water for 1 hour and 37.25 grams of n-octylamine were then added from a dropping funnel. The resulting mixture was heated to reflux and stirred for 24 hours. The reaction mixture was then filtered, washed with 1500 ml of hot water and dried in air overnight. An x-ray diffraction pattern of the powder from this reaction indicated a layer (d) spacing of 31.5 angstroms. The solid was then stirred in tetraethylorthosilicate (5 g TEOS g/solid) for 72 hours at 80° C. The material was filtered, air dried, and calcined for 4 hours at 500° C. An x-ray diffraction pattern of this powder exhibited a low angle d-spacing of 27.6 angstroms. The thickness of the $Ca_2Nb_3O_{10}$ layer was approximately 12.0 angstroms, leaving an interlayer opening of 15.6 angstroms.

EXAMPLE 64

Preparation of Layered Titanometallates Cs($NO_3$) (53.62 g, 0.2751 mole),

Ni($NO_3$)$_2$.6$H_2O$ (40.00 g, 0.1375 mole), and $TiO_2$ (51.81 g, 0.6482 mole) were ground to a homogenous mixture. The solids were heated in air to 420° C. for three hours followed by firing at 1000° C. for 12 hours. An x-ray powder pattern of the product agreed with the literature reported for the isostructural compound, $Rb_{0.7}(Mn_{0.7}Ti_{1.3})O_4$ given by Reid, et al.,Id. (Interlayer distance=8.41 A).

The materials set out in Table 5 were also synthesized by fusion of a metal oxide, alkali carbonate or nitrate and $TiO_2$; or an alkali metallate and $TiO_2$.

TABLE 5

| Reagent Stoichiometry | Metal Oxide | Fusion Temp., °C. | Lowest X-Ray Line, | |
|---|---|---|---|---|
| | | | 2 Theta | d (A) |
| $Cs_{0.7}(Mn_{0.7}Ti_{1.3})O_4$ | $CsMnO_4$ | 1000 | 10.3 | 8.57 |

TABLE 5-continued

| Reagent Stoichiometry | Metal Oxide | Fusion Temp., °C. | Lowest X-Ray Line, 2 Theta | d (A) |
|---|---|---|---|---|
| $Cs_{0.7}(Sc_{0.7}Ti_{1.3})O_4$ | $Sc_2O_3$ | 1000 | 10.3 | 8.57 |
| $Cs_{0.7}(Mg_{0.35}Ti_{1.65})O_4$ | MgO | 1000 | 10.3 | 8.57 |
| $Rb_{0.7}(Mn_{0.7}Ti_{1.3})O_4$ | $RbMnO_4$ | 900 | 11.10 | 7.97 |
| $K_{0.8}(Ni_{0.4}Ti_{1.6})O_4$ | $Ni(NO_3)_2$ | 1050 | 11.4 | 7.76 |
| $K_{0.8}(Cu_{0.4}Ti_{1.6})O_4$ | $Cu(OH)_2$ | 1050 | 11.3 | 7.83 |

Additional layered titanometallates were prepared. Reagents, reagent stoichiometries, reaction temperatures, and dwell times are displayed in Table 6 below. The reactions were carried out by thoroughly grinding the reagents to homogenous mixtures and firing in ceramic crucibles. In cases where potassium was used as the alkali metal cation, regrinding and refiring was required to obtain the layered phase in reasonable purity for further reactions. The stiff powders obtained were ground to roughly 100 mesh before further reactions.

TABLE 6

Preparation of Layered Titanometallate

| Reagent stoichiometry | Reagents | Rxn Conditions[a] | Product analysis | d (A)[b] |
|---|---|---|---|---|
| $Cs_{0.70}(Ni_{0.35}Ti_{1.65})O_4$ | $Cs_2CO_3$, $Ni(NO_3)_2$, $TiO_2$ | 420° C., 200 min<br>1000° C., 720 min | $Cs_{0.57}(Ni_{0.32}Ti_{1.70})O_4$ | 8.41 |
| $K_{0.80}(Zn_{0.40}Ti_{1.60})O_4$ | $K_2CO_3$, ZnO, $TiO_2$ | 900° C., 200 min<br>1050° C., 720 min<br>regrind, refire | $K_{0.66}(Zn_{0.35}Ti_{1.49})O_4$ | 7.83 |
| $K_{0.80}(Mg_{0.40}Ti_{1.60})O_4$ | $K_2CO_3$, MgO, $TiO_2$ | 900° C., 200 min<br>1000° C., 720 min<br>regrind, refire | $K_{0.73}(Mg_{0.39}Ti_{1.62})O_4$ | 7.83 |
| $K_{0.80}(Mn_{0.80}Ti_{1.20})O_4$ | $KMnO_4$, $TiO_2$ | 920° C., 600 min<br>1100° C., 720 min | $K_{0.69}(Mn_{0.79}Ti_{1.23})O_4$ | 7.76 |
| $K_{0.80}(Fe_{0.80}Ti_{1.20})O_4$ | $K_2CO_3$, $Fe_2O_3$, $TiO_2$ | 900° C., 200 min<br>1000° C., 720 min | $K_{0.69}(Fe_{0.73}Ti_{1.28})O_4$ | 7.90 |
| $Cs_{0.70}(Al_{0.70}Ti_{1.30})O_4$ | $Cs_2CO_3$, $Al_2O_3$, $TiO_2$ | 420° C., 180 min<br>1000° C., 720 min | $Cs_{0.72}(Al_{0.53}Ti_{1.42})O_4$ | 8.84 |

[a]All firings were carried out in air.
[b]d-layer spacing from x-ray powder diffraction data.

EXAMPLE 65

Propping Layered Titanometallate by Ion Exchange with Octylammonium Chloride The interlayer openings in the materials prepared in Example 64 were propped by exchange of the alkali metal cations with octylammonium ion. Excess octylamine (5 mole equiv/mole equiv of layered metal oxide) was slowly added to a solution of 12% HCl (4.9 equiv HCl/mole layered metal oxide) while keeping the temperature of the reaction mixture below 50° C. The layered titanometallate was then added to the octylammonium chloride solution and the mixture was heated to reflux for 24 hours.

The reaction mixture was cooled, filtered, and washed with hot distilled $H_2O$ (1.5 times the volume of the reaction solution). The solid was air dried at room temperature. Table 7 below sets out the composition and the d-spacings of the lowest two theta peak in the X-ray diffraction pattern of the propped materials.

TABLE 7

| Composition of n-Octylammonium-Exchanged Titanometallates | | |
|---|---|---|
| Composition[a,b] | % N | d(A)[c] |
| $H_3O^+{}_{0.34}Cs_{0.22}(NH_3R^+)_{0.16}[Mg_{0.35}Ti_{1.76}]O_4$ | 0.98 | 25.2 |
| $H_3O^+{}_{0.30}Rb_{0.07}(NH_3R^+)_{0.43}[Mn_{0.79}Ti_{1.39}]O_4$ | 2.24 | 24.5 |
| $H_3O^+{}_{0.43}Cs_{0.23}(NH_3R^+)_{0.10}[Mn_{0.76}Ti_{1.37}]O_4$ | 0.60 | 23.2 |
| $H_3O^+{}_{0.33}Cs_{0.12}(NH_3R^+)_{0.21}[Al_{0.66}Ti_{1.38}]O_4$ | 1.25 | 24.5 |
| $H_3O^+{}_{0.11}Cs_{0.14}(NH_3R^+)_{0.44}[Ni_{0.35}Ti_{1.75}]O_4$ | 2.40 | 23.9 |
| $H_3O^+{}_{0.39}K_{0.15}(NH_3R^+)_{0.37}[Mg_{0.46}Ti_{1.69}]O_4$ | 2.04 | 25.2 |
| $H_3O^+{}_{0.33}K_{0.03}(NH_3R^+)_{0.56}[Zn_{0.46}Ti_{1.75}]O_4$ | 2.68 | 24.6 |
| $H_3O^+{}_{0.15}K_{0.19}(NH_3R^+)_{0.43}[Fe_{0.78}Ti_{1.39}]O_4$ | 2.31 | 24.5 |
| $H_3O^+{}_{0.31}K_{0.17}(NH_3R^+)_{0.34}[Mn_{0.82}Ti_{1.30}]O_4$ | 1.97 | 24.8 |

[a]R = $C_8H_{17}$
[b]$H_3O+$ content was determined by subtracting Cs and $NH_3R$ content from the total charge required to balance the negative charge of the metal-titanium layer.
[c]d-layer spacing from lowest two theta peak in x-ray diffraction pattern.

EXAMPLE 66

Treatment of Swelled Titanometallates with Tetraethylorthosilicate

The octylammonium-exchanged solids of Example 65 were then stirred in EtOH for 2 hours, filtered, and air dried at room temperature for 2 hours. The solids were then slurried with $H_2O$ using a blender to ensure maximum mixing of the hydrophobic solid with water. The slurry was then transferred to a beaker and stirred overnight. The mixture was filtered and air dried for 4 hours.

The resulting filter cake was treated with tetraethylorthosilicate (TEOS) (5 g TEOS/g solid) for 72 hours. The pillared material was obtained by filtering this slurry and drying the solid in air. Calcination of the pillared material at 500° C. for about 4 hours in air eliminated octylamine and produced the molecular sieve. Analysis of the materials thus treated are set out in Table 8 below. The X-ray diffraction pattern of the pillared $Cs_{0.57}(Ni_{0.32}Ti_{1.70})O_4$ material is set out in FIG. 3.

TABLE 8

Titanometallates Containing Interspathic Polymeric Silica

| M | Starting Layered Titanometallate | Interlayer Opening (A)[a] | % metal | % $SiO_2$ | Residual[b] Cation A (%) |
|---|---|---|---|---|---|
| Ni | $Cs_{0.57}(Ni_{0.32}Ti_{1.70})O_4$ | 15.7 | 7.2 | 23.2 | 7.1 |
| Mg | $K_{0.73}(Mg_{0.39}Ti_{1.62})O_4$ | 14.9 | 5.2 | — | 2.9 |
| Zn | $K_{0.66}(Zn_{0.35}Ti_{1.49})O_4$ | 14.6 | 12.9 | — | 0.45 |
| Al | $Cs_{0.72}(Al_{0.53}Ti_{1.42})O_4$ | 10.2 | 9.9 | 8.5 | 8.3 |
| Fe | $K_{0.69}(Fe_{0.73}Ti_{1.28})O_4$ | 8.6 | 16.1 | 19.6 | 3.0 |

TABLE 8-continued

Titanometallates Containing Interspathic Polymeric Silica

| M | Starting Layered Titanometallate | Interlayer Opening (A)[a] | % metal | % SiO$_2$ | Residual[b] Cation A (%) |
|---|---|---|---|---|---|
| Mn | K$_{0.69}$(Mn$_{0.79}$Ti$_{1.23}$)O$_4$ | 5.5 | 19.9 | 21.3 | 2.6 |

[a] d spacing from powder diffraction minus thickness of metal oxide layer
[b] A = alkali metal atom content in molecular sieve.

What is claimed is:

1. A method for preparing a layered material containing an interspathic polymeric chalcogenide of at least one element selected from Groups IB, IIB, IIIA, IIIB, IVA, IVB, VA, VB, VIA, VIIA, and VIIIA of the Periodic Table, which method comprises: treating a layered chalcogenide of at least one element having an atomic number of 4, 5, 12 to 15, 20 to 33, 38 to 51, 56 to 83 and greater than 90, inclusive, which contains ion exchange sites having interspathic cations associated therewith, with an organic compound which is a cationic species or capable of forming a cationic species to effect exchange with said interspathic cations; providing between the layers of said treated layered chalcogenide, an electrically neutral compound capable of conversion to said interspathic polymeric chalcogenide; and converting said compound to the interspathic polymeric chalcogenide to form said layered material.

2. The method of claim 1 wherein said interspathic polymeric chalcogenide is an interspathic polymeric oxide and said layered chalcogenide is a layered oxide.

3. The method of claim 1 wherein said layered material is exposed to elevated temperatures in order to remove organic compounds therefrom.

4. The method of claim 2 wherein said layered material is exposed to elevated temperatures in order to remove organic compounds therefrom.

5. The method of claim 1 wherein said cationic species is an alkylammonium cation having at least 3 carbon atoms.

6. The method of claim 5 wherein said alkylammonium cation is derived from an n-alkyl primary monoamine.

7. The method of claim 6 wherein said compound capable of conversion is hydrolyzable and said converting occurs by hydrolysis to form said layered material.

8. The method of claim 7 wherein said converting comprises calcination.

9. The method of claim 2 wherein said converting comprises calcination.

10. The method of claim 2 wherein said interspathic cations are selected from the group consisting of H$^+$ and H$_3$O$^+$, said layered oxide of a metal contains an element selected from the group consisting of titanium, zirconium and hafnium, and said interspathic polymeric oxide comprises an oxide of an element selected from the group consisting of silicon, germanium, tin and lead.

11. The method of claim 10 wherein said layered material is exposed to elevated temperatures in order to remove organic compounds therefrom.

12. The method of claim 10 wherein said layered oxide of a metal contains titanium, and said interspathic polymeric oxide is an oxide of silicon.

13. The method of claim 12 wherein said layered material is exposed to elevated temperatures in order to remove organic compounds therefrom.

14. The method of claim 2 wherein said interspathic cations comprise alkali metal cations, said layered oxide of a metal contains an element selected from the group consisting of titanium, zirconium and hafnium, and said interspathic polymeric oxide comprises an oxide of an element selected from the group consisting of silicon, germanium, tin and lead.

15. The method of claim 14 wherein said layered material is calcined in order to remove organic compounds therefrom.

16. The method of claim 14 wherein said interspathic cations comprise Na$^+$, said layered oxide of a metal contains titanium, and said interspathic polymeric oxide is an oxide of silicon.

17. The method of claim 16 wherein said layered material is calcined in order to remove organic compounds therefrom.

18. The method of claim 7, wherein said hydrolyzable compound is selected from the group consisting of tetraethylorthosilicate, tetramethylorthosilicate and tetrapropylorthosilicate.

19. The method of claim 7 wherein said hydrolyzable compound is tetraethylorthosilicate.

20. The method of claim 7 wherein said alkylammonium cation is C$_3$ or larger alkylammonium.

21. The method of claim 7 wherein said alkylammonium cation is n-octylammonium.

22. The method of claim 7 wherein said alkylammonium cation is n-dodecylammonium.

23. The method of claim 7 wherein said alkylammonium cation is n-heptylammonium.

24. The method of claim 7 wherein said alkylammonium cation is n-hexylammonium.

25. The method of claim 7 wherein said alkylammonium cation is n-propylammonium.

26. The method of claim 1 wherein said interspathic polymeric chalcogenide is amorphous.

27. The method of claim 1 wherein said interspathic polymeric chalcogenide is crystalline.

28. The method of claim 3 wherein said layered material is ion-exchanged.

29. The method of claim 28 wherein said layered material is ion-exchanged with a cation selected from the group consisting of cesium, cerium, cobalt, nickel, copper, zinc, manganese, platinum, lanthanum, aluminum, ammonium and hydronium.

30. The method of claim 3 wherein said interspathic polymeric chalcogenide comprises an oxide of an element selected from the group consisting of Si, Ti, B, Al, Zr, Ta, Nb, V, and Mg.

31. The method of claim 3 wherein said interspathic polymeric chalcogenide comprises an oxide of an element selected from the group consisting of silicon and aluminum.

32. The method of claim 7 wherein said hydrolyzable compound is selected from the group consisting of tetraalkylsilicate, aluminum alkoxide, boron alkoxide and titanium alkoxide.

33. The method of claim 32 wherein said hydrolyzable compound is selected from the group consisting of tetraethylorthosilicate and titanium alkoxide.

34. The method of claim 2 wherein said layered oxide is non-swellable.

35. The method of claim 4 wherein said layered oxide is non-swellable.

36. The method of claim 2 wherein said layered oxide is a clay.

37. The method of claim 2 wherein said layered oxide comprises a layered silicate.

38. The method of claim 4 wherein said layered oxide comprises a layered silicate.

39. The method of claim 2 wherein said layered oxide is a high silica alkali silicate.

40. The method of claim 2 wherein said layered oxide is selected from the group consisting of magadiite, natrosilite, kenyaite, makatite, nekoite, kanemite, okenite, dehayelite, macdonaldite and rhodesite.

41. The method of claim 40 wherein said layered material is calcined to remove organics.

42. The method of claim 37 wherein said layered silicate is magadiite.

43. The method of claim 37 wherein said layered silicate is makatite.

44. The method of claim 37 wherein said layered silicate is kenyaite.

45. The method of claim 37 wherein said layered silicate contains non-silicon framework atoms.

46. The method of claim 45 wherein said layered silicate is kenyaite.

47. The method of claim 46 wherein said non-silicon framework atoms include those selected from the group consisting of B, Al and Zr.

48. The method of claim 45 wherein said layered silicate is magadiite.

49. The method of claim 48 wherein said non-silicon framework atoms are selected from the group consisting of Al, Cr, Fe, and Ni.

50. The method of claim 49 wherein said non-silicon framework atoms comprise Al.

51. The method of claim 49 wherein said non-silicon framework atoms comprise Fe.

52. A thermally stable composition comprising a non-swellable layered chalcogenide of an element having an atomic number of 4, 5, 12 to 15, 20 to 33, 38 to 51, 56 to 83 and greater than 90, inclusive, said layered metal chalcogenide comprising an interspathic polymeric chalcogenide of an element selected from Groups IB, IIB. IIIA, IIIB, IVA, IVB, VA, VB, VIA, VIIA, and VIIIA of the Periodic Table.

53. The composition of claim 52 wherein said layered chalcogenide is a layered oxide and said interspathic polymeric chalcogenide is an interspathic polymeric oxide.

54. The composition of claim 53 wherein said layered oxide comprises an oxide of a metal selected from the group consisting of silicon, titanium, zirconium, and hafnium.

55. The composition of claim 54 wherein said layered oxide comprises a titanium oxide and said polymeric oxide comprises polymeric silica.

56. The composition of claim 54 wherein said layered oxide comprises a titanium oxide and said polymeric oxide comprises polymeric alumina.

57. The composition of claim 54 wherein said layered oxide comprises a titanium oxide and said polymeric oxide comprises polymeric titania.

58. The composition of claim 55 wherein said layered oxide initially comprises $Ti_3O_7^=$.

59. The composition of claim 56 wherein said layered oxide initially comprises $Ti_3O_7^=$.

60. The composition of claim 57 wherein said layered oxide initially comprises $Ti_3O_7^=$.

61. The composition of claim 53 wherein said layered oxide comprises silicon oxide and said polymeric oxide comprises polymeric silica.

62. The composition of claim 61 wherein said layered oxide comprises magadiite.

63. The composition of claim 61 wherein said layered oxide comprises makatite.

64. The composition of claim 61 wherein said layered oxide comprises kenyaite.

65. The composition of claim 53 wherein said layered oxide comprises silicon oxide and said polymeric oxide comprises polymeric alumina.

66. The composition of claim 65 wherein said layered oxide comprises magadiite.

67. The composition of claim 53 wherein said layered oxide comprises silicon oxide and said polymeric oxide comprises polymeric titania.

68. The composition of claim 67 wherein said layered oxide comprises magadiite.

69. The composition of claim 61 wherein said layered oxide comprises framework elements selected from the group consisting of Al, B, Cr, Fe, Ga, Ni and Zr.

70. The composition of claim 62 wherein said layered oxide comprises framework elements selected from the group consisting of Al, B, Cr, Fe, Ga, Ni and Zr.

71. The composition of claim 61 wherein said layered oxide comprises framework elements comprising Al.

72. The composition of claim 61 wherein said layered oxide comprises framework elements comprising Fe.

73. The composition of claim 61 wherein said layered oxide comprises framework elements of Ni.

74. The composition of claim 64 wherein said layered oxide comprises framework elements selected from the group consisting of Al, B, Cr, Fe, Ga and Ni.

75. The composition of claim 74 wherein said layered oxide comprises framework elements of Al.

76. A thermally stable composition comprising a layered chalcogenide of an element having an atomic number of 4, 5, 12 to 15, 20 to 33, 38 to 51, 56 to 83 and greater than 90, inclusive, said layered metal chalcogenide comprising an interspathic polymeric chalcogenide of an element selected from Group IVB of the Periodic Table, and said composition having a d-spacing greater than about 20 angstroms.

77. The composition of claim 76 wherein said layered metal chalcogenide is a layered metal oxide and said interspathic polymeric chalcogenide is an interspathic polymeric oxide.

78. The composition of claim 77 wherein said d-spacing is greater than about 30 angstroms.

79. The layered material of claim 77 wherein said layered oxide is an oxide of a metal selected from the group consisting of silicon, titanium, zirconium, and hafnium.

80. The composition of claim 77 wherein said layered oxide is a titanium oxide and said polymeric oxide comprises polymeric silica.

81. The composition of claim 77 wherein said layered oxide is a titanium oxide and said polymeric oxide comprises polymeric aluminum oxide.

82. The composition of claim 80 wherein said layered oxide is a titanium oxide and said polymeric oxide comprises polymeric titanium oxide.

83. The composition of claim 80 wherein said layered oxide initially comprises $Ti_3O_7^=$.

84. The composition of claim 77 wherein said layered oxide is a silicon oxide and said polymeric oxide is selected from the group consisting of polymeric silica, polymeric alumina and polymeric titania.

85. A layered titanate composition comprising interspathic polymeric silica, and having the X-ray diffraction pattern set out in Table 1.

86. An organic compound conversion catalyst comprising the product of claim 3.

87. An organic compound conversion catalyst comprising the product of claim 8.

88. The method of claim 1 wherein a solvent selected from the group consisting of polar organic solvents having an electric dipole moment of at least about 3.0D and water is contacted with said layered oxide prior to treating said layered oxide with said organic compound capable of forming a cationic species.

89. The method of claim 88 wherein said polar organic solvent has an electric dipole moment of at least about 3.5D.

90. The method of claim 88 wherein said polar organic solvent comprises dimethylsulfoxide.

91. The method of claim 1 wherein a solvent selected from the group consisting of polar organic solvents having an electric dipole moment of at least about 3.0D and water is contacted with said layered oxide during the treating of said layered oxide with an organic compound capable of forming a cationic species.

92. The method of claim 91 wherein said polar organic solvent has an electric dipole moment of at least about 3.5D.

93. The method of claim 91 wherein said polar organic solvent is dimethylsulfoxide.

94. The method of claim 1 wherein said organic cation is subsequently exchanged with a larger organic cation.

95. The layered material prepared by the method of claim 1.

96. The layered material prepared by the method of claim 2.

97. The layered material prepared by the method of claim 3.

98. The layered material prepared by the method of claim 4.

99. The layered material prepared by the method of claim 6.

100. The layered material prepared by the method of claim 7.

101. The layered material prepared by the method of claim 12.

102. The layered material prepared by the method of claim 13.

103. The composition of claim 74 wherein said layered oxide comprises framework elements of B.

* * * * *